(12) United States Patent
Banerjee et al.

(10) Patent No.: US 7,582,488 B2
(45) Date of Patent: Sep. 1, 2009

(54) GEL-SHELL BEADS WITH ADSORBED OR BOUND BIOMOLECULES

(75) Inventors: Sukanta Banerjee, Pennington, NJ (US); Enqing Tan, Lexington, MA (US)

(73) Assignee: Bio Array Solutions Ltd., Warren, NJ (US)

(*) Notice: Subject to any disclaimer, the term of this patent is extended or adjusted under 35 U.S.C. 154(b) by 0 days.

(21) Appl. No.: 10/973,700

(22) Filed: Oct. 26, 2004

(65) Prior Publication Data

US 2005/0112655 A1 May 26, 2005

Related U.S. Application Data

(60) Provisional application No. 60/515,079, filed on Oct. 28, 2003.

(51) Int. Cl.
*G01N 33/544* (2006.01)
*G01N 33/545* (2006.01)
*G01N 33/546* (2006.01)
*C08F 220/18* (2006.01)

(52) U.S. Cl. .......... 436/535; 436/531; 436/534; 526/329.7

(58) Field of Classification Search .......... 435/7.1, 435/177, 182, 962; 436/518, 524–525, 527–533, 436/535–540; 524/916; 530/413
See application file for complete search history.

(56) References Cited

U.S. PATENT DOCUMENTS

| | | | | |
|---|---|---|---|---|
| 4,143,203 A | * | 3/1979 | Rigopulos et al. | 428/407 |
| 4,421,896 A | * | 12/1983 | Dorman | 525/54.1 |
| 4,891,324 A | * | 1/1990 | Pease et al. | 436/519 |
| 5,241,012 A | * | 8/1993 | Clark | 525/333.6 |
| 5,573,909 A | * | 11/1996 | Singer et al. | 435/6 |
| 5,637,508 A | * | 6/1997 | Kidwell et al. | 436/525 |
| 5,763,198 A | * | 6/1998 | Hirth et al. | 435/7.21 |
| 5,840,485 A | * | 11/1998 | Lebl et al. | 435/6 |
| 6,193,951 B1 | * | 2/2001 | Ottoboni et al. | 424/9.5 |
| 6,268,222 B1 | * | 7/2001 | Chandler et al. | 436/523 |
| 6,838,289 B2 | * | 1/2005 | Bell et al. | 436/172 |
| 7,229,840 B1 | * | 6/2007 | Wischerhoff | 436/518 |
| 2003/0152931 A1 | * | 8/2003 | Chiou et al. | 435/6 |
| 2004/0014073 A1 | * | 1/2004 | Trau et al. | 435/6 |

FOREIGN PATENT DOCUMENTS

| | | |
|---|---|---|
| EP | 0 179 039 | 4/1986 |
| WO | WO 01/94947 | 12/2001 |
| WO | WO 03/079401 | 9/2003 |

OTHER PUBLICATIONS

Lofas et al. Methods for site controlled coupling to carboxymethyldextran surfaces in surface plasmon resonance sensors. Biosensors & Bioelectronics (1995), vol. 10, pp. 813-822.*
Suzawa et al. "Adsorption of Plasma Proteins Onto Polymer Latices" Advances in Colloid and Interface Science vol. 35 (1991), 139-172.*
Elaissari et al. "Hydrophilic and cationic latex particles for the specific extraction of nucleic acids" J. Biomater. Sci. Polymer End. vol. 10 (1999), 403-420.*
Trau et al. "Nanoencapsulated Microcrystalline Particles for Superamplified Biochemical Assays"Anal. Chem., 74 (21), 5480-5486, Web Release Date: Sep. 25, 2002.*
D. Proudnikov et al., "Immobilization of DNA in Polyacrylamide Gel for the Manufacture of DNA and DNA-Oligonucleotide Microchips" Analytical Biochemistry 259: 34-41 (1998).
G. Yershov et al., "DNA Analysis and Diagnostics on Oligonucleotide Microchips" Proc. Natl Acad. Sci. USA 93:4913-18 (1996).

* cited by examiner

*Primary Examiner*—Christopher L Chin
*Assistant Examiner*—Christine Foster
(74) *Attorney, Agent, or Firm*—Eric P. Mirabel

(57) ABSTRACT

Disclosed are gel-coated beads (including Hydrogel™-coated beads), which are capable of adsorbing, or absorbing, proteins and other biomolecules onto or into the gel coating. The gel-coated beads with absorbed or adsorbed biomolecules are suitable for use in an assays, purification or other purposes. The beads have a core made from any of a number of materials, including latex, coated with the gel shell. The biomolecules can be retained within the gel, following adsorption, by covalent attachment, or, by selection of conditions of ambient pH and/or ionic strength such that they are retained without further reaction. Therefore, adsorbed proteins would retain the ability to bind to their respective ligands.

5 Claims, 25 Drawing Sheets

EDC mediated covalent immobilization

EDC-NHS mediated covalent immobilization

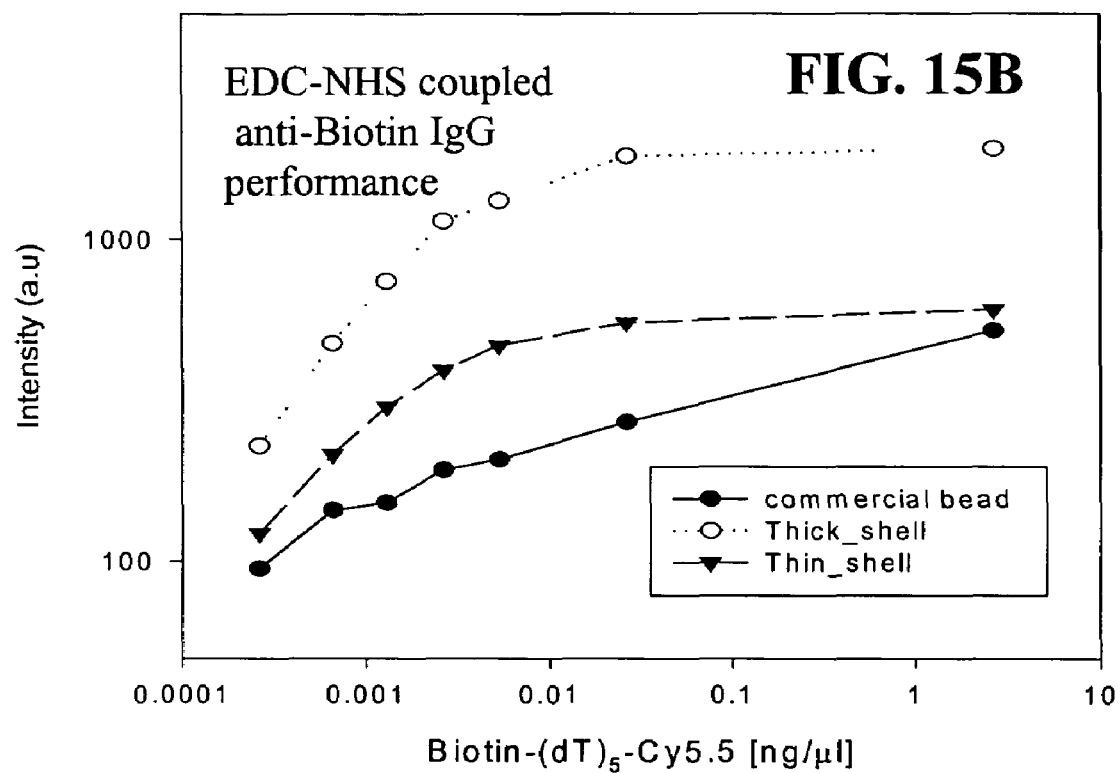
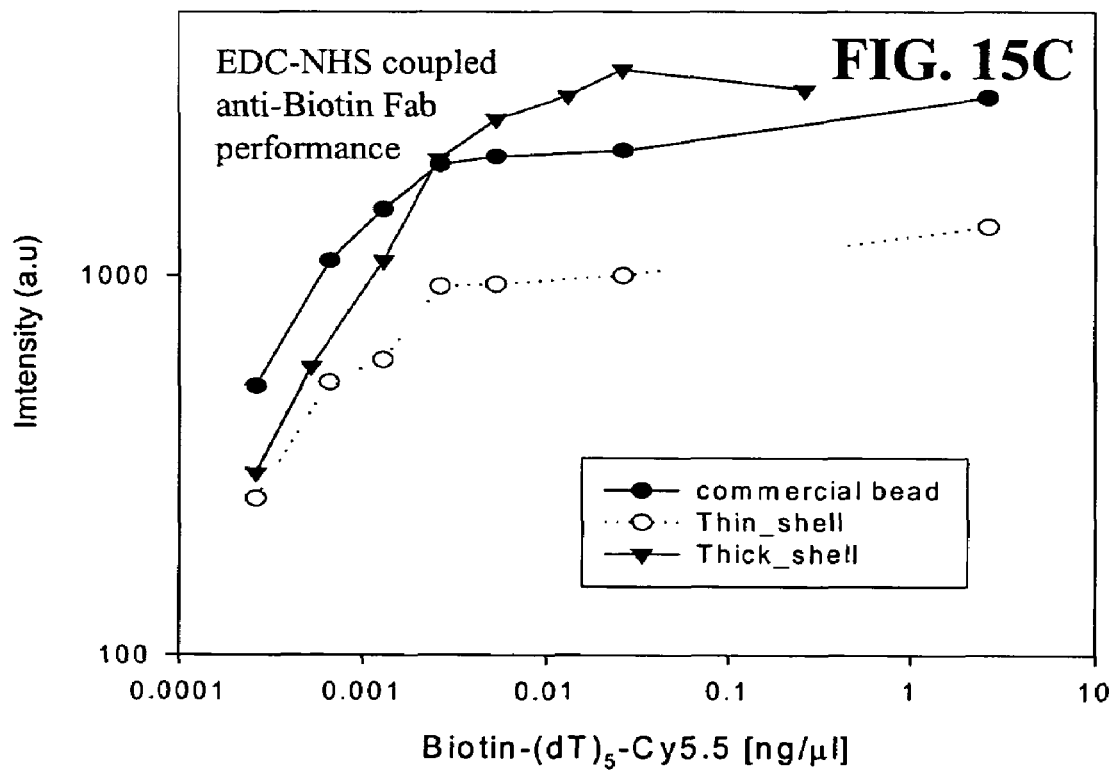

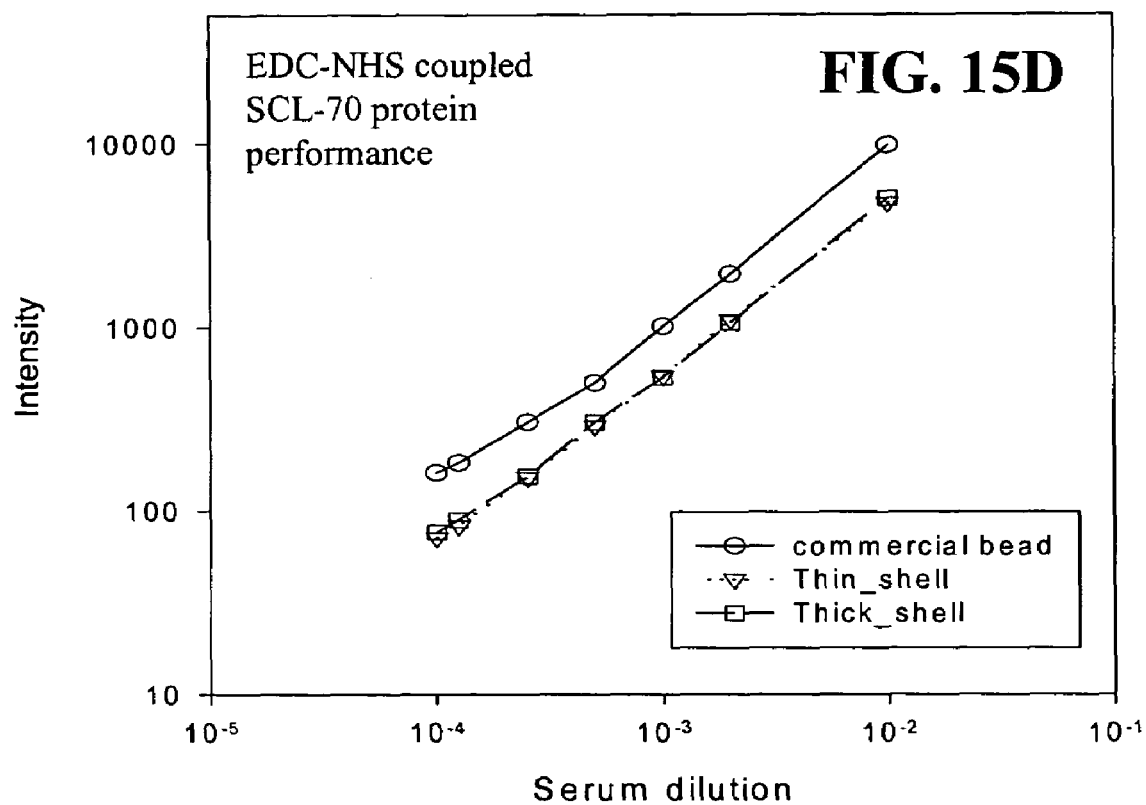
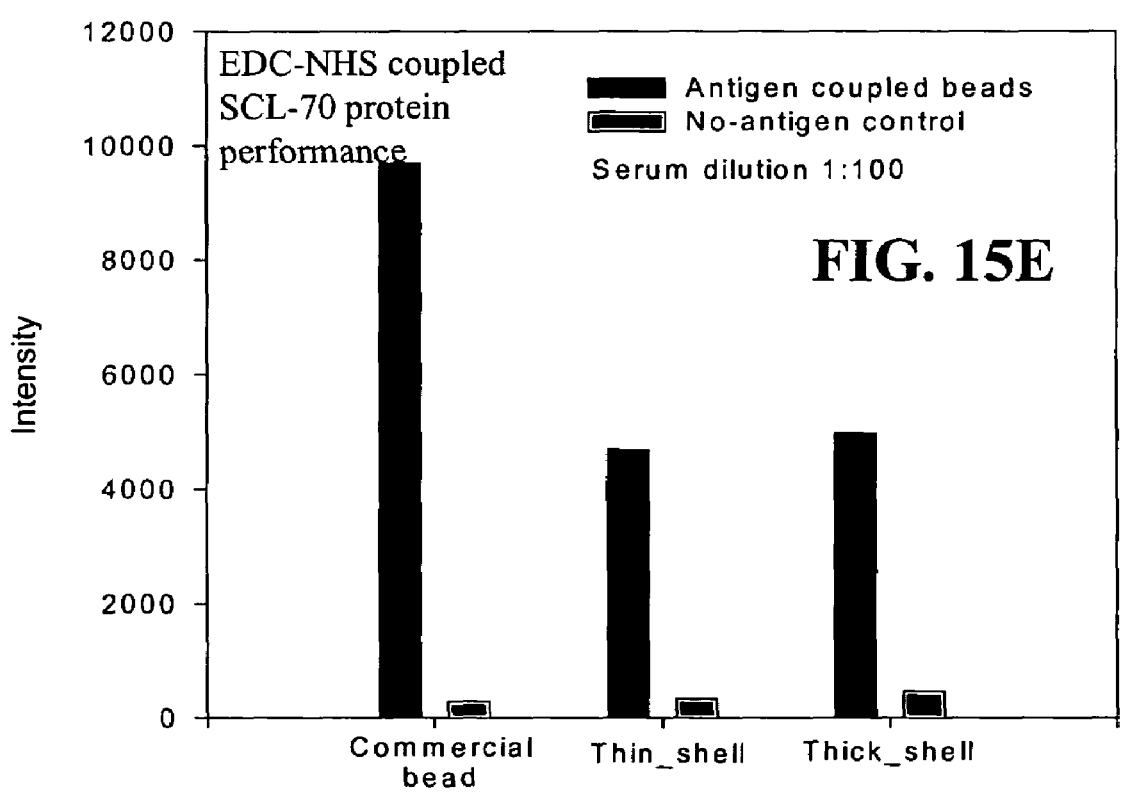

Aldehyde mediated covalent immobilization

Tosyl mediated covalent immobilization

US 7,582,488 B2

GEL-SHELL BEADS WITH ADSORBED OR BOUND BIOMOLECULES

RELATED APPLICATIONS

This application claims priority to U.S. provisional application No. 60/515,079, filed Oct. 28, 2003.

FIELD OF THE INVENTION

The invention relates to beads coated with a gel.

BACKGROUND

Microarrays are powerful tools for comprehensive analysis of biomolecule interactions, including protein-protein and oligonucleotide-oligonucleotide interactions. Such analysis is useful in molecular characterization and diagnosis of physiological or disease states and has a broad potential. In all microarrays, interactions are analyzed by first immobilizing a set of biomolecules in an array format on a slide. The slide is then probed with a set of fluorescently-labeled complementary ligands and any binding is noted.

Compared to the DNA microarrays, the fabrication of useful protein microarrays is generally more difficult and technically challenging. This is because, proteins are intrinsically fragile molecules which are sensitive to exposure to both low and high temperature, extremes of pH, presence of hydrophobic surfaces, high shear and to removal of water. It is imperative therefore that such conditions are avoided during preparation, storage and handling of protein microarrays.

A preferred solution to many of these problems is to attach proteins to encoded microbead particles, including encoded particles made of polymer resin ("Multianalyte Molecular Analysis Using Application-Specific Random Particle Arrays," U.S. application Ser. No. 10/204,799, filed on Aug. 23, 2002; WO 01/98765, incorporated by reference). The encoded capture-protein coated particles are then assembled in a 2D array format and placed in contact with samples anticipated to contain target proteins. Any binding between the capture and target proteins are then determined by the presence of a fluorescent assay signal. Particular capture proteins generating a positive assay signal can be determined by decoding the array. There are several known and commercially available methods for immobilization of proteins on microparticles (Bangs Laboratories Inc., TechNote # 205 Covalent Coupling, 2002 and TechNote # 204, Adsorption to Microspheres, 1999). Most commonly used approaches result in random covalent attachment or sticking of proteins onto microparticle surfaces, which often leads to a wrongly oriented molecule incapable of participating in binding. In addition, use of improper chemistry per se may chemically modify and hence denature the protein molecule.

Coupling proteins to surfaces using site-selective chemistry can circumvent some of these problems. In principle, such oriented attachment leaves the proteins' active sites accessible and also improves their stability (Peluso, P. et al., Analytical Biochemistry 312 (2003) 113-124). Such techniques are, however, of restricted use because they require additional protein modification, purification and concentration steps, which may be impractical for use with large numbers of unique molecules. Hence the choice of a surface chemistry and surface topology that will allow diverse types of proteins to be immobilized and yet retain their secondary structure and thus their biological activity is needed.

Hydrogels are three-dimensional hydrophilic polymeric networks capable of imbibing large quantities of water. Their high aqueous content offers a "protein-friendly" environment and they have recently received attention for their potential use as a microarray substrate (see Perkin Elmer Corp.'s website: HydroGel Application Note). Arenkov et al. (Arenkov, P. et al. Analytical Biochemistry, 278, 123-131 (2000)) reported the fabrication of arrays which were produced by immobilizing proteins in gel pads (100 μm×100 μm×20 μm) which were in turn attached to a glass slide surface. Because of three-dimensional matrix structure, the protein immobilization was reported to be very efficient. The aqueous environment helped to keep the protein in its native form and it was freely accessible for assay binding reactions. The major disadvantages of the method are a complicated fabrication process and the difficulty of removing the unbound protein from the gel pad, due to transport limitations.

None of these approaches, therefore, are sufficiently versatile to provide a broad platform for multiplexed protein-ligand interaction analysis which is compatible with the vast diversity of protein structures and functions and permits maintenance of secondary and tertiary protein structure.

SUMMARY

Disclosed are ionic gel-coated beads (including Hydrogel™-coated beads), which are capable of adsorbing, or absorbing, proteins and other biomolecules, respectively, onto or into the gel coating, suitable for use in an assays, purification or other purposes. Although the biomolecules can either be adsorbed or absorbed into the gel, and the uptake in each case would be driven by different mechanism, from a practical standpoint the result in either case is a biomolecule-loaded gel with binding sites available for ligand-binding. The assay signal generated upon binding of a ligand would be greater than if the biomolecule was bound to a bead by another method, as the binding sites tend to remain available in the adsorption/absorption to the gel (such processes hereinafter, for convenience, collectively referred to as "adsorption.") The beads, which can be referred to as core-shell beads (or core-shell particles), have a core made from any of a number of materials, including latex, coated with the ionic gel shell. The biomolecules can be retained within the gel, following adsorption, by covalent attachment, or, by selection of conditions of ambient pH and/or ionic strength such that they are retained without further reaction.

As noted above, the gel-shell beads, with proteins or other biomolecules adsorbed therein, can be used for assays. In particular, one can adsorb proteins and assay for ligands, including enzymes, antigens or antibodies, reactive with the adsorbed proteins. The properties of the gel layer are such that the epitopes and/or activity of the adsorbed receptor or capture protein is not altered or affected. Therefore, adsorbed proteins would retain the ability to bind to their respective ligands.

Also disclosed is a process for the use of gel-shell particles for selectively capturing specific nucleic acids or proteins from a crude mixture of analytes, for example, whole blood or cell lysates. The sample containing whole blood is placed in contact with the gel-shell particles which are functionalized with ligand molecules of interest. The red and white cells are automatically screened out by the gel because of their size, and only the molecules smaller than the pores in the gel can enter and bind the ligands. The components in the plasma which are small enough to enter the gel bind to the ligands, and the binding can be detected by conventional methods. The remainder of the components can be readily washed off.

In this way, the reliability of the assay results is improved, as large analytes are separated and will not generate binding events.

The gel-shell particles can also be used as microreactors, for example, in separating and increasing discrimination of different binding reactions taking place on different beads, as detected using ELISA. In a conventional spotted array with receptor-ligand complex on the surface, a binding event is detected by the presence of an enzyme typically associated with the secondary detection agent (secondary antibody, Streptavidin or like). In the presence of an appropriate substrate, the enzyme catalyzes the formation of fluorescent or colored product locally. However, the product generally tends to diffuse through the array, and smudge signals from proximal spots. This has prevented the development of microarrays with high feature density which are useful in an ELISA format. With the gel-shell particles of the invention, however, the signal from binding events can be made to remain localized within the gel shell of the particle, taking advantage of the partition coefficient difference between the substrate and the product. For example, the gel-shell could be amphiphilic and have hydrophilic and hydrophobic domains. The hydrophilic domains could serve as a reaction vessel for the enzyme and the hydrophobic domains serve to partition a fluorescent and hydrophobic product. Such a chemistry has recently been reported in literature (Kiyonaka, S. et al., Nature Materials, 3, 58-64 (2004).

The gel-shell adsorbed proteins or other biomolecules can be used as agents for one-step assay and purification of cognate ligands. In such method, the core-shell beads with the adsorbed biomolecules are packed in a windowed holding cell, and a sample including the substance to be assayed/purified is passed through the cell. The assay results can be monitored in situ through the transparent cell window, and for the purification step, the beads can be removed from the column and the protein can then be eluted from the bead using known methods.

The core-shell beads and their various uses are described further below.

BRIEF DESCRIPTION OF THE DRAWINGS

FIG. 15B shows results as determined by binding to Biotin-$(dT)_5$-Cy5.5 of coupling of mouse Anti-Biotin mAb to a functionalized gel-shell using an EDAC-NHS protocol.

FIG. 15C shows results as determined by binding to Biotin-$(dT)_5$-Cy5.5 of coupling of mouse Anti-Biotin-Fab to a functionalized gel-shell using an EDAC-NHS protocol.

FIGS. 15D and 15E show results as determined by a labeled detection antibody from coupling of SCL-70 to a functionalized gel-shell using an EDAC-NHS protocol.

DETAILED DESCRIPTION

Figure 1A:
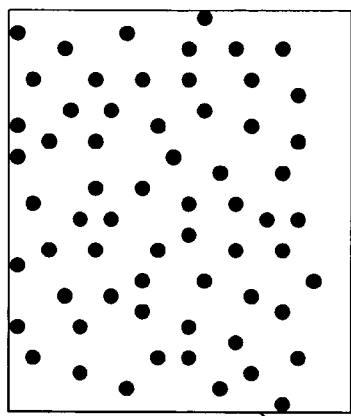
FIG. 1A depicts (dispersing the gel-shell beads of the invention in an appropriate buffer.)
Figure 1B:
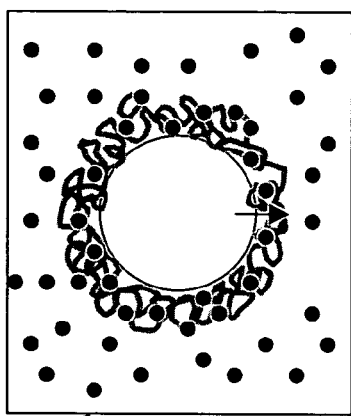
FIG. 1B depicts subjecting the mixture of beads to the step of biomolecule immobilization.
Figure 1C:
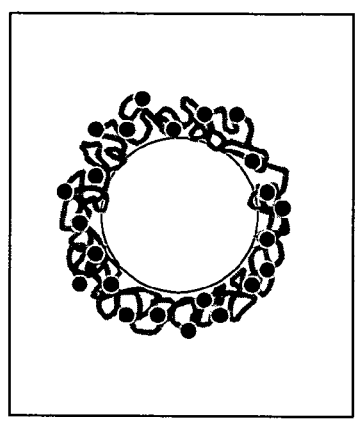
FIG. 1C depicts seperating the free biomolecules from the beads and re-dispersing the beads in the buffer of choice.
Figure 1D:
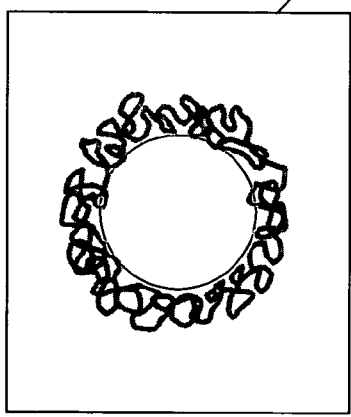
FIG. 1D (depicts adding an aqueous or buffered solution of the biomolecule to be immobilized to the bead suspension.)

The process for the preparation of gel coated (gel-shell) beads carrying tethered or physically imbibed proteins or other biomolecules which retain a high degree of biological activity, is carried out as follows:
(i) Dispersing the gel-shell beads of the invention in an appropriate buffer (FIG. 1A);
(ii) Adding an aqueous or buffered solution of the biomolecule (FIG. 1D) to be immobilized to the bead suspension;
(iii) Subjecting the mixture to the step of biomolecule immobilization (FIG. 1B and FIG. 1E); and
(iv) Separating the free biomolecules from the beads and re-dispersing the beads in the buffer of choice (FIG. 1C and FIG. 1F).

Any polymer may be used to provide the core polymer particles provided a stable dispersion of the polymer particles is available. Suitable polymers include homopolymers or copolymers, where copolymers include polymers formed of two or more monomer units, and including polymers formed of three or more monomer units, sometimes referred to as "terpolymers". Hydrophobic polymers, including polymers including monomers of the vinyl class, that is, monomers containing the vinyl group, are preferred, including those having a styrene group. One group of preferred polymers includes polystyrene or polystyrene copolymers containing from about 50% to about 100% by weight styrene monomer units. The polymer optionally may be cross-linked or uncross-linked. In one embodiment, the microparticle is formed of polystyrene cross-linked with 1% divinylbenzene, based on the weight of the microparticle. In another embodiment, the microparticle comprises styrene/methacrylic acid copolymer containing from about 0.6 to about 1% methacrylic acid, based on the weight of the microparticle.

Suitable polymeric materials include, by way of example and not by way of limitation, polymers including the following monomers:
acrylic acid, or any ester thereof, such as methyl acrylate, ethyl acrylate, propyl acrylate, butyl acrylate, 2-ethyl hexyl acrylate or glycidyl acrylate;
methacrylic acid, or any ester thereof, such as methyl methacrylate, ethyl methacrylate, propyl methacrylate, butyl methacrylate, lauryl mathacrylate, cetyl methacrylate, stearyl mathacrylate, ethylene glycol dimethacrylate, tetraethylene glycol dimethacrylate, glycidyl methacrylate or N,N-methacryloxy hydroxy propyl)-(hydroxy alkyl) amino ethyl amidazolidinone;
allyl esters such as allyl methacrylate;
itaconic acid, or ester thereof;
crotonic acid, or ester thereof;
maleic acid, or ester thereof, such as dibutyl maleate, dioctyl maleate, dioctyl maleate or diethyl maleate;
styrene, or substituted derivatives thereof such as ethyl styrene, butyl styrene or divinyl benzene;
monomer units which include an amine functionality, such as dimethyl amino ethyl methacrylate or butyl amino ethyl methacrylate;
monomer units which include an amide functionality, such as acrylamide or methacrylamide;
vinyl-containing monomers such as vinyl ethers; vinyl thioethers; vinyl alcohols; vinyl ketones; vinyl halides, such as vinyl chlorides; vinyl esters, such as vinyl acetate or vinyl versatate; vinyl nitriles, such as acrylonitrile or methacrylonitrile;
vinylidene halides, such as vinylidene chloride and vinylidene fluoride;
tetrafluoroethylene;
diene monomers, such as butadiene and isoprene; and
allyl ethers, such as allyl glycidyl ether.

Suitable polymeric materials may include, by way of example and not by way of limitation the following polymers: polyoxides, such as poly(ethylene oxide) and poly(propylene oxide); polyesters, such as poly(ethylene terepthalate); polyurethane; polysulfonate; polysiloxanes, such as poly(dimethyl siloxane); polysulfide; polyacetylene; polysulfone; polysulfonamide; polyamides such as polycaprolactam and poly(hexamethylene adipamide); polyimine; polyurea; heterocyclic polymers such as polyvinylpyridine and polyvinyl pyrrolidinone; naturally occurring polymers such as natural rubber, gelatin, cellulose; polycarbonate; polyanhydride; and polyalkenes such as polyethylene, polypropylene and ethylene-propylene copolymer.

The polymeric material may contain functional groups such as carboxylates, esters, amines, aldehydes, alcohols, or halides which provide sites for the attachment of chemical or biological moieties desirable to enhance the utility of the particles in chemical or biological analyses. Methods for preparing microparticles from such polymers are well known in the art. Representative procedures for preparing core microparticles are set forth in the Examples below.

The gel-shell may be formed by any polymer-coating technique. Core-shell morphology of the gel-shell beads is thermodynamically favored if the shell-forming polymer exhibits higher polarity, or lower interfacial tension than does the core-forming polymer. Core-shell morphology also is favored if the volume fraction of the shell-forming polymer is greater than that of the core-forming polymer. Thus, synthesis of core-shell particles is performed at a shell/core weight ratio greater than 1. In certain embodiments, the core polymer is hydrophobic and the gel-shell polymer is relatively hydrophilic and carries functional groups of interest.

Within these constraints, any monomer or combination of monomers may be selected as the gel-shell polymer. A mixture of vinyl monomers is preferred. According to one embodiment of the invention, a monomer mixture of methyl methacrylate as the major constituent, and hydroxyethyl methacrylate and methacrylic acid as minor constituents, is used to form a shell over a polystyrene or modified polystyrene core. One such monomer mixture is composed of by weight about 6% hydroxyethyl methacrylate, from about 5% to about 20% methacrylic acid, the balance being methyl methacrylate. These monomers are more hydrophilic than polystyrene.

Bead size may be selected as appropriate for the intended end use. Typically, particles will range in size from about 0.1 to about 100 microns in diameter, more typically from about 0.5 to about 50 microns, even more typically from about 1 to about 10 microns. Preferably, the beads are "monodisperse", that is, beads in a set have a narrow size range, preferably displaying a coefficient of variation of the mean diameter ("CV") of no more than about 5%.

The gel-shell beads may be rendered magnetically responsive by incorporation of an appropriate magnetic material, in the core or in the shell, according to well-known procedures.

According to one such method, particles are coated with a ferrofluid, such as a ferrofluid described in Example 17. By "magnetically responsive" as used herein means the ability to change location or orientation in response to application of a magnetic field.

The gel-shell beads may also be rendered fluorescent by incorporation of a fluorescent dye. The dye may comprise any dye that imparts an optically detectable color or fluorescence. The color or fluorescence may be detectable with the naked eye or with the aid of a microscope or other optical instrument. When more than one dye is used, the dyes can be selected so that they have substantially different absorption spectra, emission spectra or emission lifetimes.

Following gel-shell bead synthesis, the biomolecule of interest are placed in contact with the gel-shell beads. When the gel-shell is contacted with a solution containing a solute, such as a biomolecule, the biomolecule partitions between the gel and the surrounding liquid. The partition coefficient of a biomolecule in a charged, pH-sensitive gel is influenced by solution properties such as pH, temperature and ionic strength, and material properties such as gel composition, charge density, crosslinking, and polymer fraction in the hydrogel. Changes in any one of these parameters affects the three major mechanisms which contribute to partitioning in a charged hydrogel: size exclusion, electrostatics, and short range interactions such as hydrophobicity. Partitioning of large biomolecules into a gel is dependent on the gel's porosity. However, the porosity or pore diameter present in a gel cannot be readily determined, since commonly used fabrication methods do not lead to large, permanent pores. Rather, porosity is a result of temporary spacing between the flexible, mobile, hydrated polymer chains. Higher swelling, therefore, undoubtedly favors higher partition coefficients for large biomolecules. One problem in the case of macroscopic gels is that the transport of molecules to and from the gel is often controlled by diffusion and hence is a slow process. In the present case, however, the transport in and out of the gel-shell is fast because the characteristic time for diffusion is proportional to the square of the shell thickness, and the shell thickness is only a fraction of a micron. In addition to porosity, electrostatics and electrokinetic effects play a dominant role in protein partitioning in charged gels. The forces of interaction between a swollen charged gel and a protein can be either net-attractive or net-repulsive, depending on whether the pH is less than or greater than the pI of the protein and whether the protein is charged oppositely to the gel. High gel charge density and opposite charge of the protein and gel favor higher partitioning due to electrostatic interactions.

According to this invention the immobilization of the biomolecule of interest may be performed by a physical imbibition step as described above followed by covalent coupling (see FIG. 1B using any one of the well-known coupling reactions such as carbodiimide coupling, aldehyde coupling or tosyl ester coupling (see below). Other methods of coupling using esters, alcohols, amines, thiols, halides, hydrazides or epoxide can be used as well by methods well known in the art.

Figure 1E:
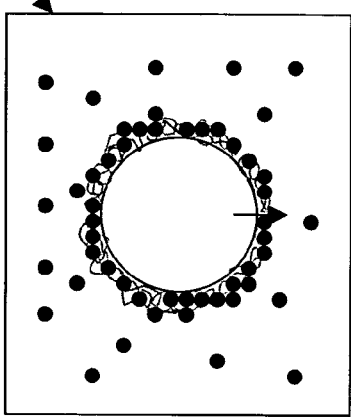
FIG. 1E depicts subjecting the mixture of beads and to the step of biomolecule immobilization.
Figure 1F:
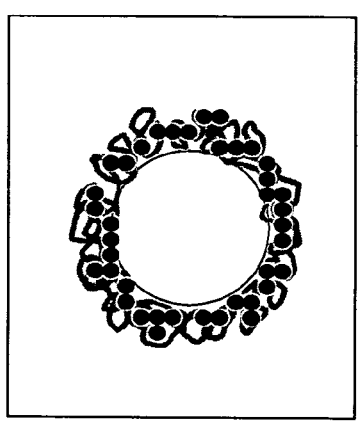
FIG. 1F depicts separating the free biomolecules from the beads and re-dispersing the beads in the buffer of choice.

Alternatively, after initial biomolecule imbibition a collapse transition may be initiated utilizing a stimuli-sensitive gel-shell, effectively physically trapping the imbibed biomolecules (See FIG. 1E). Stimuli-sensitive gels are polymers that respond with discrete transition in equilibrium volume to small changes in their environment. Such gels can be classified according to the stimuli they respond to, such as: temperature-, pH-, ionic strength-, light-, electric- or magnetic field-sensitive. Such gels have been widely researched as potential scaffolds for tissue engineering and controlled release of pharmaceutical proteins (N. A. Peppas: Hydrogels in Medicine and Pharmacy, Vol. 1. Fundamentals, CRC Press, Boca Raton, Fla., 1986, 180 pages, N. A. Peppas: Hydrogels in Medicine and Pharmacy, Vol. 2. Polymers, CRC Press, Boca Raton, Fla., 1987, 172 pages and N. A. Peppas: Hydrogels in Medicine and Pharmacy, Vol. 3. Properties and Applications, CRC Press, Boca Raton, Fla., 1987, 196 pages) and as chromatographic support media for separation and purification of proteins (Sassi, A. P. et al. AICHE Journal 42(8): 2335-2353 (1996)). In a collapsed gel, a low degree of swelling also favors high partitioning of the proteins, but the partitioning in this regime is driven by a different mechanism. Increased polymer concentration in the shrunken gel layer results in attractive polymer-protein interactions (predominantly short-range interactions such as hydrophobic interactions). Several methods have been reported in the literature to tune the collapse transition pH of a pH-sensitive gel. For example, for incorporation of hydrophobic moieties into a polyacrylic acid based gel, the pH at which the collapse occurs could be tuned from 5 to 7 (Philippova, O. et al. Macromolecules, 30, 8278-8285 (1997)). In addition, partitioning due to hydrophobic interactions often leads to irreversible trapping of the protein molecule in the hydrogel (Sukhishvili, S. A., and Granick S. J. Chem. Phys. 110, 20, 10153-10161 (1999)), which makes any post-partitioning covalent reaction to immobilize the proteins unnecessary.

EXAMPLES

I. Preparation of Particles

Example 1

Preparation of Polymer Core Particles

Polymer particles suitable for coating with Hydrogel were prepared as follows. A 250 ml round bottom glass flask, equipped with a reflux condenser and an $N_2$ inlet-outlet adapter and agitator, was placed in a thermostated water bath. The flask was charged with a solution of 4.2 g of polyvinylpyrolidone (Aldrich, MW ~29, 000) and 106 g of ethyl alcohol (Aldrich, 200 proof, 99.5%). The flask contents were heated to 70° C., and 26 g of styrene (Aldrich, 99+%) and 0.156 g methacrylic acid (Aldrich, 99%) was added. Both, styrene and methacrylic acid were freshly purified by vacuum distillation. The polymerization was started by adding 0.265 g of 2,2'-azobisisobutyronitrile (Aldrich, 89%) dissolved in 10 g ethanol. The agitation speed was 200 rpm and the reaction time 24 h. At the end of reaction, the system was cooled at room temperature. The monomer conversion, measured gravimetrically, was 81.7%. The latex was centrifuged at 1,000 rpm for 15 min. and the supernatant was removed. The polymer particles were cleaned 3 times by re-dispersion in ethanol and centrifugation. Then, the polymer was re-dispersed in a mixture of 1:1 0.2% polyvinylpyrolidone and 0.02% of bis(2-ethylhexyl) sulfosuccinate sodium salt (Fluka, 99.0%) in distilled water, mixed and centrifuged for 20 min. at 2,000 rpm. This operation was repeated and finally, the particles were suspended in the same mixture of emulsifier solution. The latex solid content was 16.9%. Monodisperse polystyrene particles having an average number diameter of 2.78±0.06 μm with the CV 2.0%, measured by SEM, were obtained.

To generate larger diameter core particles, the same procedure was used as above, except 0.25 g of 2,2'-Azobisisobutyronitrile in 10 g ethanol were used for starting the polymerization. After 22 hours, the reaction was stopped by cooling, and the conversion of monomers was measured as 89.0%. The latex was cleaned and finally formulated as 21.9% solids. The particle diameter was measured by SEM and it was found 3.08±0.11 μm with a CV of 3.5%.

Example 2

Synthesis of Gel-Shell Particles Having Shell/Core Weight Ratio of 1.0 (Thick-Shell)

The particles prepared above were coated with Hydrogel using the following procedure, to generate thick-shell core shell beads. To 49.4 g latex particles, having a particle diameter 2.78μ and a solids content of 16.9% (prepared as in the example above) was added 8.33 g of methyl methacrylate containing 6% hydroxyethyl methacrylate and 20% methacrylic acid along with 0.21 g of t-butyl peroxy-2-ethylhexanoate (Luperox 26, ATOFINA). The mixture was placed in a 250 ml screw cap glass bottle and shaken for at least 0.5 h. Then, 0.21 g of $CuCl_2.2H_2O$ dissolved in 16.67 g of a 1:1 mixture of 0.2% PVP and 0.02% of bis(2-ethylhexyl) sulfosuccinate sodium salt in distilled water was added, followed by addition of 0.27 g of sodium formaldehyde sulfoxylate (Aldrich), 0.014 g ethylene diaminetetracetate-iron sodium complex (Aldrich) in 3.3 g solution of the same 1:1 mixture of 0.2% polyvinyl pyrolidone and 0.02% bis(2-ethylhexyl) sulfosuccinate sodium salt. The bottle was placed in a water bath shaker which was at 45° C. The reaction was run for 6 h. The latex was filtered through 100 μm nylon filter and centrifuged at 1000 rpm for 20 min. The supernatant was removed and the particles were cleaned, several times, with 0.1% Tween solution of pH 10, by mixing in a roller for 10 h, followed by centrifugation and decantation. Finally the particles were suspended in 0.1% Tween solution. The mean particle diameter was 3.29 um±0.06 and the CV was 1.9%.

Example 3

Synthesis of Gel Shell Particles Having Shell/Core Weight Ratio of 0.5 (Thin-Shell)

To generate thin-shell core shell beads, the procedure was similar to that described immediately above, except that the core particle had a 3.08 um diameter (as was described in the prior example) and the specific amounts of the ingredients was different. In summary, 57.2 g of latex prepared as in the prior example (21.9% solids) was mixed with 4.17 g methyl methacrylate containing 6% hydroxyethyl methacrylate and 20% methacrylic acid along with 0.107 g of t-butyl peroxy-2-ethylhexanoate. 0.1 g of $CuCl_2.2H_2O$ dissolved in 16.67 g of 1:1 mixture of 0.2% PVP and 0.02% of bis(2-ethylhexyl) sulfosuccinate sodium salt in distilled water was added, followed by addition of 0.15 g of sodium formaldehyde sulfoxylate, 0.007 g ethylene diaminetetracetate-iron sodium complex dissolved in 3.3 g solution of the same 1:1 emulsifier mixture. The latex particles had a diameter of 3.23 um±0.08 and the CV was 2.7%.

II. Passive Adsorption of Protein to Gel-Shell Beads Under Various Conditions

In the Examples below, the protein was adsorbed into the Hydrogel coating on the beads. It is seen that for adsorption under certain conditions (low pH and low salt concentration, or high salt concentration), the protein can be retained in the Hydrogel shell, and will not passively diffuse out even after the conditions are altered. The pH and ionic strength can be chosen to be in a range that will not affect interaction of the adsorbed protein with its ligand.

Example 4

Temperature Dependence of Passive Adsorption of Protein onto Thin-Shell Beads

Experiments were performed to examine the temperature effect on passive adsorption of protein onto thin-shell beads using recombinant protein L ("Pro-L," from Sigma Chemical Co.). Distinct fluorescently-dyed thin-shell beads were washed and mixed with Pro-L at concentrations of 25, 100, 400, and 1600 μg per mg beads. The reactions were carried out in 500 μL of PBS (phosphate buffered saline, pH=3, adjusted by adding HCl) under three temperature conditions each for 4 hours—room temperature (approximately 25° C.), 37° C., and 50° C. The Pro-L coated beads were then incubated with 500 μL storage buffer (PBS, pH=7.2, 0.1% BSA and 0.1% Azide) overnight at room temperature for blocking purpose. These beads were stored individually at 4° C. until they were used.

Figure 2:
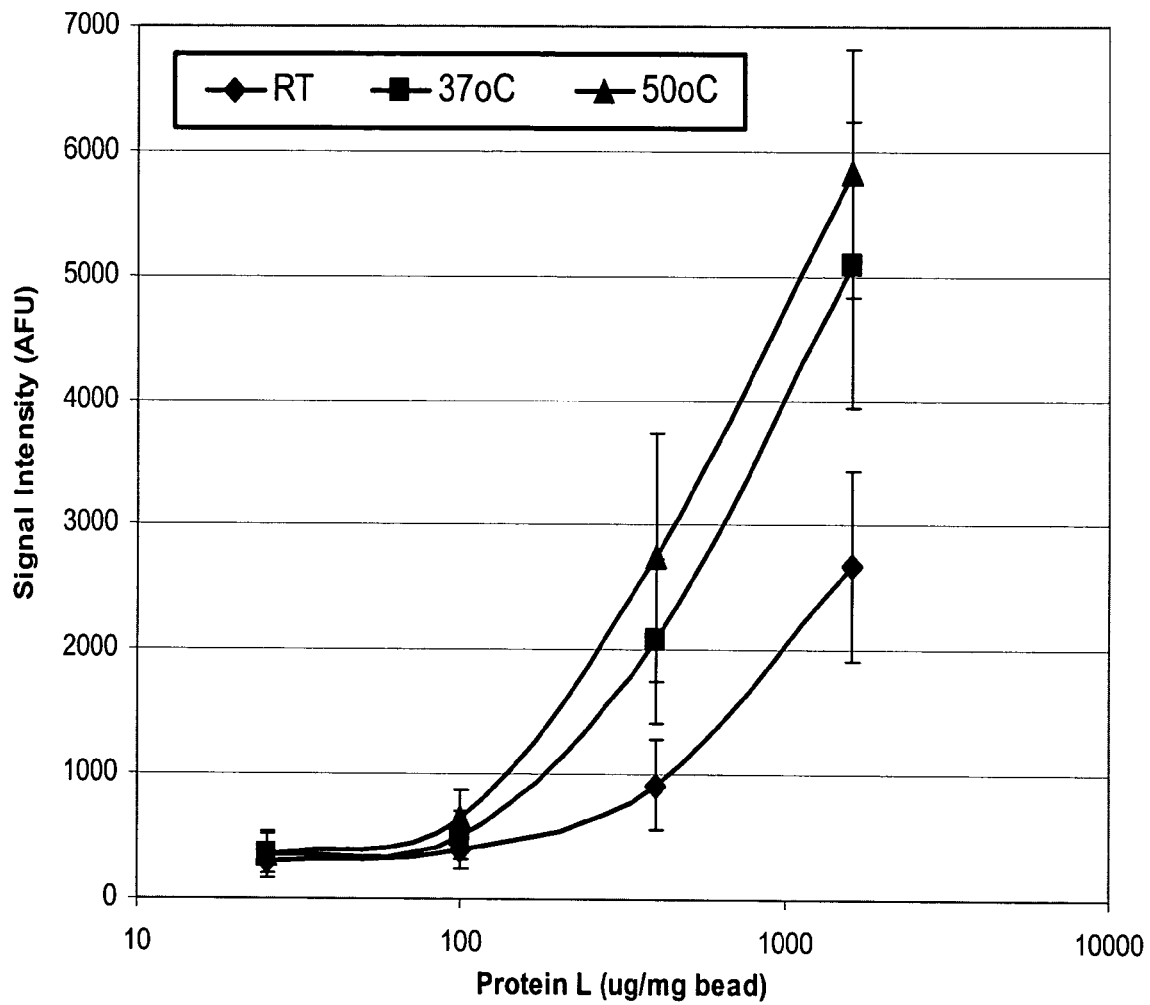
FIG. 2 plots signal intensity from Protein L immobilized on gel-shell beads against concentration of Protein L at three different temperatures.

Since Protein L has a high binding affinity to human immunoglobulins, the coupling efficiency was indirectly monitored by measurements of the human IgG binding activity of each bead type. The Pro-L-coated beads were mixed and assembled on a silicon chip, which was then contacted with a human serum sample (AAB224 from SLR Research, 1-50 dilution) to allow the interaction of Pro-L and human IgG molecules. After removing non-specifically bound antibodies, a goat anti-human IgG specific antibody-Cy5 conjugate was used to visualize the antibodies captured. The decoding and assay images were acquired using a microscope installed with a CCD camera. The assay signals were extracted and analyzed. FIG. 2 shows: (1) the antibody binding activity increases in a concentration-dependent manner, with the highest activity observed with beads coupled at 1600 μg Pro-L per mg beads; (2) the antibody binding activity also increases in a temperature-dependent manner, with the highest activity observed with beads coated at 50° C., the highest temperature tested. The signal intensity reflects the amount of protein coupled onto each bead.

These results suggest that higher temperature conditions (up to about 50° C.) facilitates protein adsorption onto thin-shell beads.

Procedure for Protein L coupling to Thin-Shell beads:
1. Add 10 uL of 1% beads (10 ug) into a tube containing 500 uL PBSLT, mix by vortexing.
2. Spin down the beads at 10000 rpm for 3 min and discard the supernatant.
3. Re-suspend the beads in 500 uL PBSLT, vortex to mix.
4. Spin down the beads at 10000 rpm for 3 min and discard the supernatant.
5. Re-suspend the beads in 500 uL PBS pH=3.
6. Add the proper amount of protein L each tube. Vortex to mix.
7. Incubate at proper temperature for 4 hours while rotating.
8. Spin down the beads at 10000 rpm for 3 min and discard the supernatant.
9. Wash once with 500 uL storage buffer.
10. Resuspend in 500 uL storage buffer, incubate at RT for overnight while rotating.
11. Spin down the beads at 10000 rpm for 3 min and discard the supernatant.
12. Wash once with 500 uL storage buffer.
13. Resuspend in 2× volume of starting volume.
14. Store at 4° C. for use.

Example 5

Time Dependence of Passive Adsorption of Protein onto Gel-Shell Beads

An experiment was performed to examine the effect of time passage on passive adsorption of protein L (Pro-L) onto thin-shell beads. Distinct fluorescently-dyed thin-shell beads were washed, re-suspended in 500 μL of PBS (pH=3), and mixed with Pro-L at concentration of 100 μg per mg beads by adding 64 μL of in a total volume of 564 μL. The reactions were carried out at 37° C. incubator while rotating for 15 min, 30 min, 1 hr, 2 hr, 3 hr and 4 hrs. The Pro-L coated beads were then incubated with 500 μL storage buffer (PBS, pH=7.2, 0.1% BSA and 0.1% Azide) overnight at room temperature for blocking purpose. These beads were stored individually at 4° C. until they were used.

Figure 3:
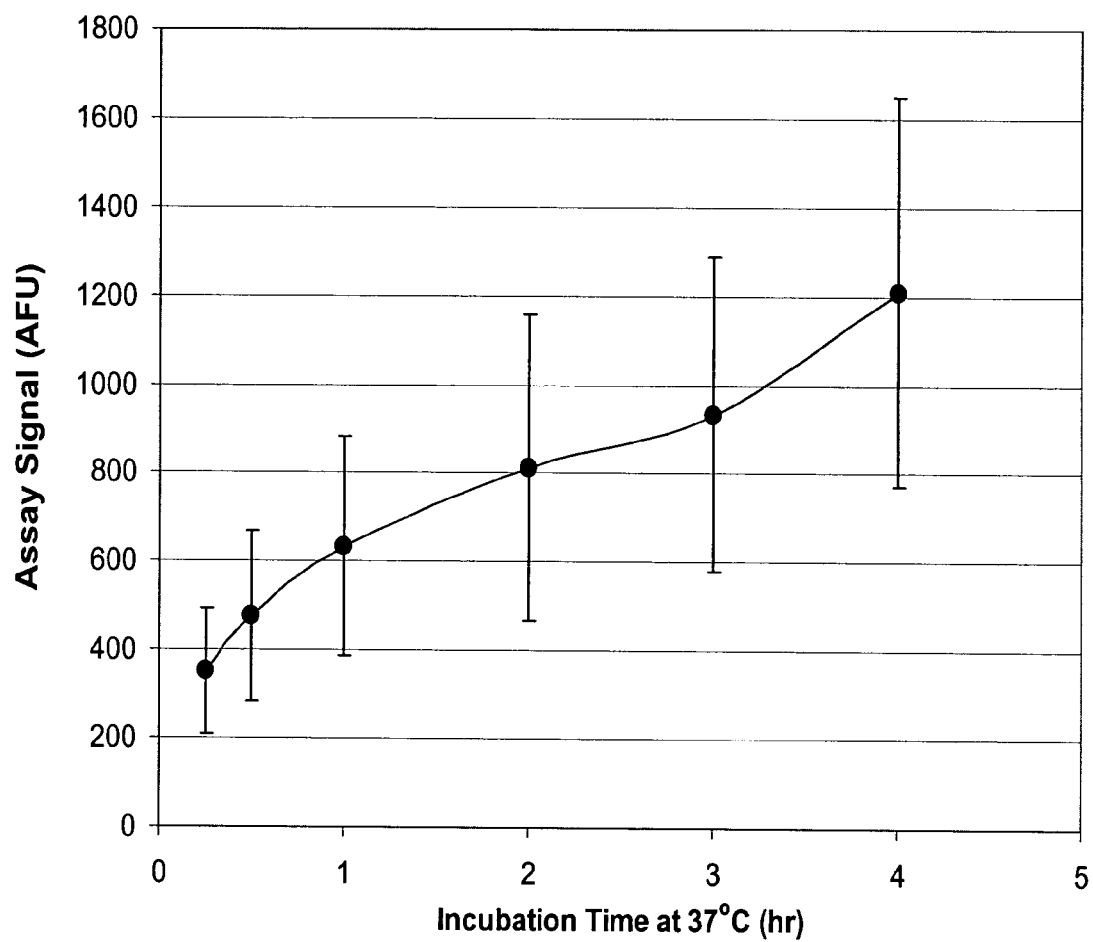
FIG. 3 plots signal intensity from Protein L immobilized on gel-shell beads against the time Protein L was incubated with the beads.

The Pro-L-coated beads were mixed and assembled on a silicon chip, which was then contacted with a human serum sample (AAB224 from SLR Research, 1-50 dilution) to allow the interaction of Pro-L and human IgG molecules. After removing non-specific bound antibodies, a goat anti-human IgG specific antibody-Cy5 conjugate was used to visualize the antibodies captured. The decoding and assay images were acquired using a microscope installed with a CCD camera. The assay signals were extracted and analyzed. FIG. 3. shows that the antibody binding activity correlates with the length of time of protein adsorption. The antibody binding activity starts to appear at 15 min with a peak level after 4 hours of incubation, the longest time tested.

Example 6 pH Dependence of Passive Adsorption of Protein onto-Gel-Shell Beads

The pH effect on passive adsorption of protein onto thin-shell beads was assessed using Pro-L and human serum samples. Protein was coupled to distinct fluorescently-encoded thin-shell beads through passive adsorption. The reactions were carried out in phosphate buffered saline with different pH (namely, 3, 5, 7, 9, and 11) at 37° C. for 4 hours. The Pro-L coated beads were then incubated in storage buffer containing BSA (PBS, pH=7.2, 0.1% BSA and 0.1% Azide) for 60 min at RT. Pro-L coupled beads were re-suspended in storage buffer and stored individually at 4° C. until they were used.

Figure 4A:
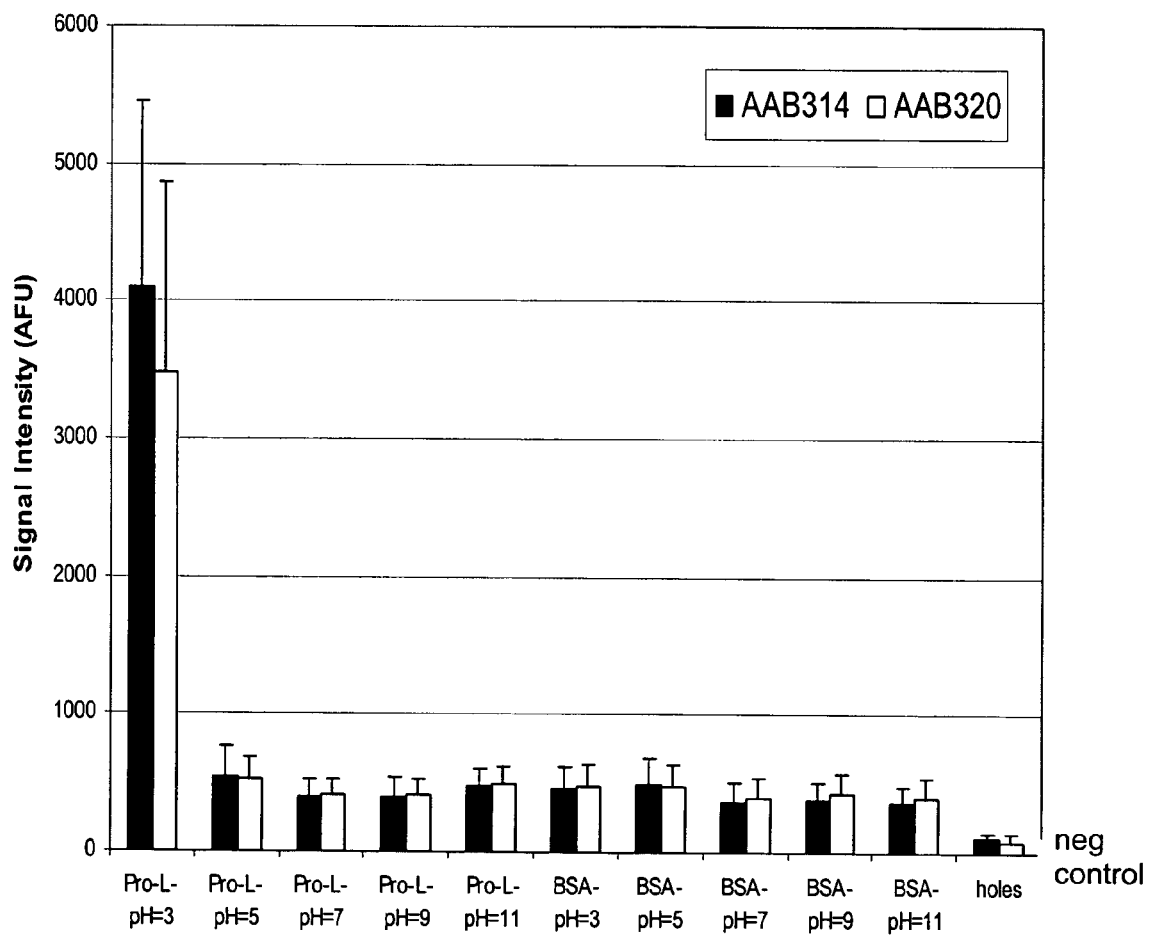
FIG. 4A plots signal intensity from Protein L immobilized at various pHs on gel-shell beads and also the signal intensity for BSA incubated with the gel-shell beads at various pHs.

The beads coupled with Pro-L were mixed and assembled on silicon chips which were subsequently incubated with two human serum samples for 30 min at room temperature. After removing non-specific binding, the beadchips were then incubated with fluorescently labeled detection antibodies (goat anti-human IgG specific antibody-Cy5 conjugate) for 15 min at room temperature to visualize the amount of IgG molecules captured by each individual bead. The decoding and assay images were acquired using a microscope installed with a CCD camera. The assay signals were then extracted and analyzed. FIG. 4A shows that the highest IgG-capturing activity was observed with beads coupled at pH 3 and no significant activity was observed with any of the BSA (negative control) coated beads. These results indicate that low ionic strength (pH=3) facilitates passive adsorption.

Figure 5:
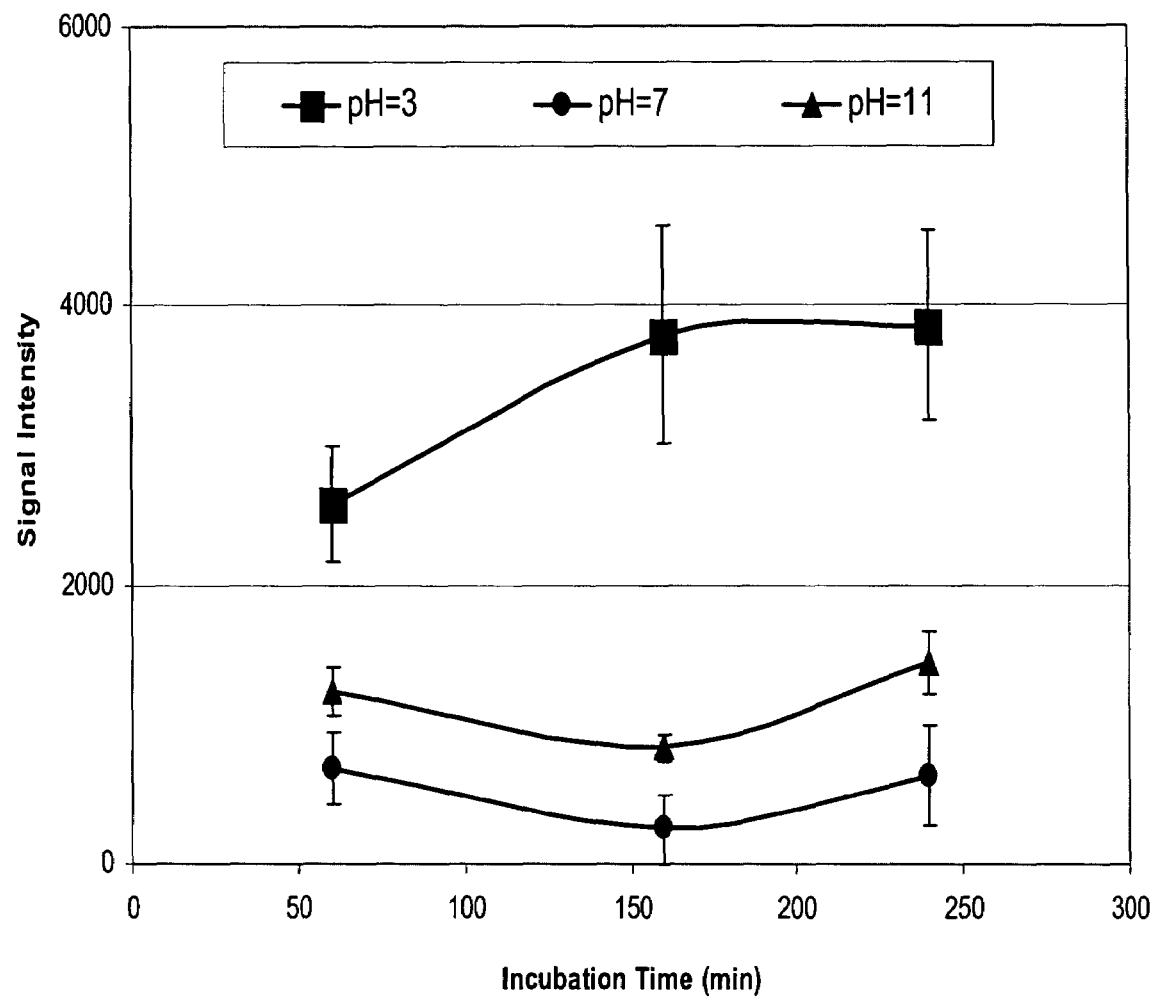
FIG. 5 plots signal intensity from goat anti-human IgA antibody-Cy5 conjugate immobilized at various pHs on gel-shell beads against the time the protein was incubated with the beads.

Similarly, in a separate experiment involving thick-shell beads, the passive adsorption of fluorescently labeled protein (goat anti-human IgA antibody-Cy5 conjugate) performed at acidic buffer (pH=3) resulted in significant higher fluorescent signal intensities compared with beads coupled at neutral (pH=7) or alkaline (pH=11) buffer. Since the dye-protein complex was immobilized and visualized with no second step assay, the signal intensity reflects the actual amount of protein coupled onto each bead (FIG. 5).

Figure 4B:
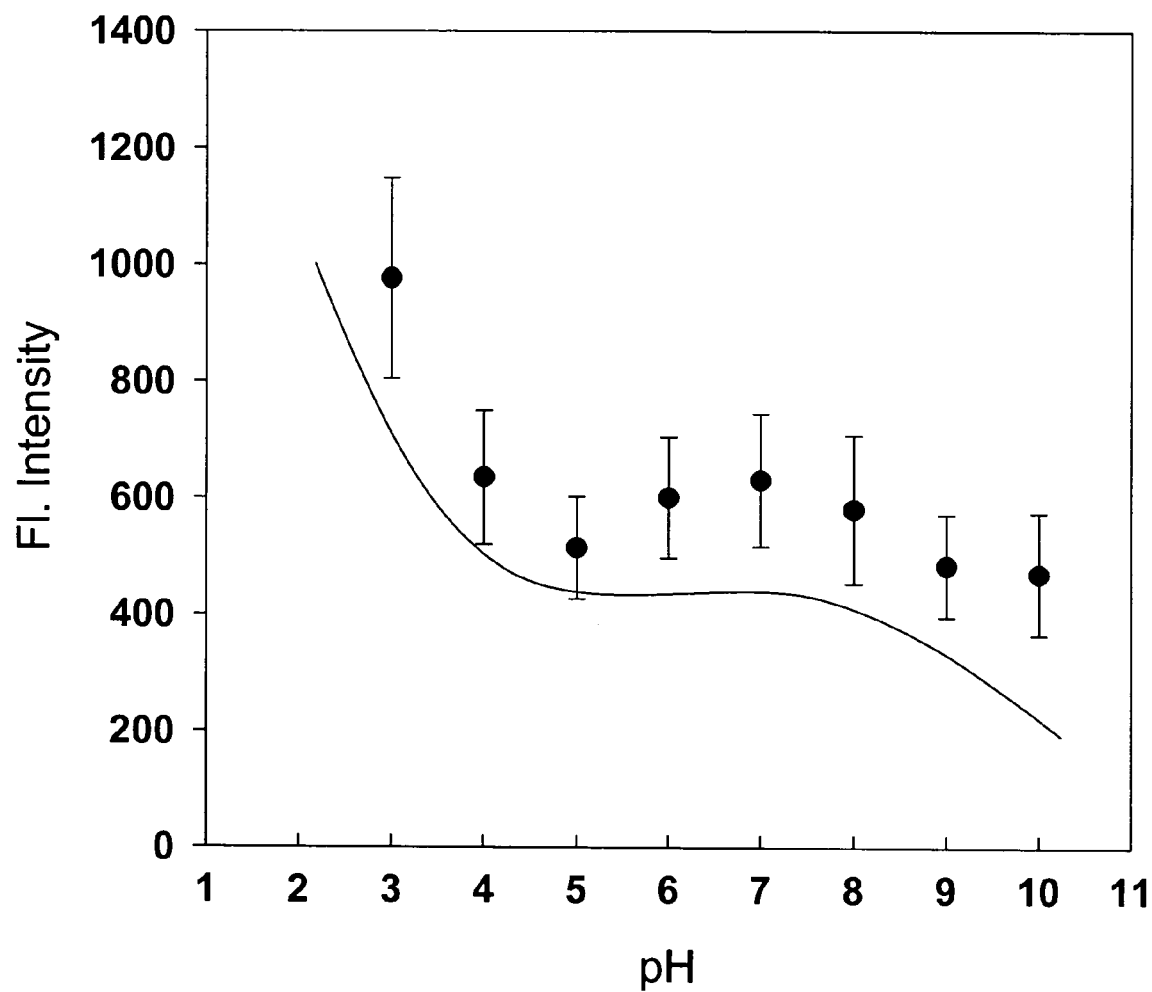
FIG. 4B is the graph demonstrating the signal intensity v. pH for the histograms in FIG. 4A.

A similar experiment was carried out using Bodipy-FL labeled Avidin (a protein with high pI value of 10) obtained from Molecular Probes, OR. Briefly, 500 μg of washed thin gel-shell beads were incubated with 500 μg of labeled protein suspended in 500 ul of 50 mM NaCl solution at the appropriate pH (the pH was adjusted using dilute HCl or NaOH). The mixture was incubated for one hour and then the beads were separated by centrifugation, washed and stored in phosphate buffered saline. For analysis a small aliquot of the beads were taken, assembled on a chip and their green fluorescence recorded. FIG. 4B shows a plot of the green on-bead fluorescence recorded as a function of pH. As seen before, there is clear indication of enhanced protein uptake at pH=3.

All the experimental evidence supports that the passive adsorption of proteins onto thin or thick shell beads is better achieved with acidic buffer condition than neutral or alkaline buffer conditions. Therefore, this acidic buffer was used for passive adsorption of other proteins.

Procedure for Pro-L coupling to thin-shell beads at different pH levels:

1. Add 10 uL of 1% beads (10 ug) into a tube containing 500 uL PBSLT, mix by vortexing.
2. Spin down the beads at 10000 rpm for 3 min and discard the supernatant.
3. Re-suspend the beads in 500 uL PBSLT, vortex to mix.
4. Spin down the beads at 10000 rpm for 3 min and discard the supernatant.
5. Re-suspend the beads in 500 uL PBS with different pHs (3, 5, 7, 9, 11).
6. Add the proper amount of protein L each tube. Vortex to mix.
7. Incubate at 37° C. for 4 hours while rotating.
8. Spin down the beads at 10000 rpm for 3 min and discard the supernatant.
9. Wash once with 500 uL storage buffer.
10. Re-suspend in 500 uL storage buffer, incubate at RT for 60 min while rotating.
11. Spin down the beads at 10000 rpm for 3 min and discard the supernatant.
12. Wash once with 500 uL storage buffer.
13. Re-suspend in 2× volume of starting volume.
14. Store at 4° C. for use.

Example 7

Low Salt Effect on Passive Adsorption of Protein onto Gel-Shell Beads

To examine the salt effect on protein immobilization, Protein L, SSA-60 and Jo-1 were coupled to distinct fluorescently-encoded thin-shell beads in PBS buffers with different salt concentrations. All these buffers were adjusted to pH 3 using HCl. The reactions were carried out under three different salt concentration conditions—regular PBS (0.1M Sodium Phosphate; 0.15M Sodium Chloride); 1-10 diluted PBS (10 mM Sodium Phosphate; 15 mM Sodium Chloride) and 1-50 diluted PBS—for 4 hours at 37° C., which was followed by a 60 min incubation in storage buffer containing BSA at RT. The beads were mixed and assembled on silicon chips, which were subsequently incubated with a pooled human serum sample containing anti-SSA-60 and anti-Jo-1 antibodies, or buffer only as negative control. After removing non-specifically bound antibodies, the chips were incubated with goat anti-human IgG specific antibody-Cy5 conjugate for 15 min at RT. The decoding and assay images were acquired and the assay signals were extracted and analyzed.

Figure 6:
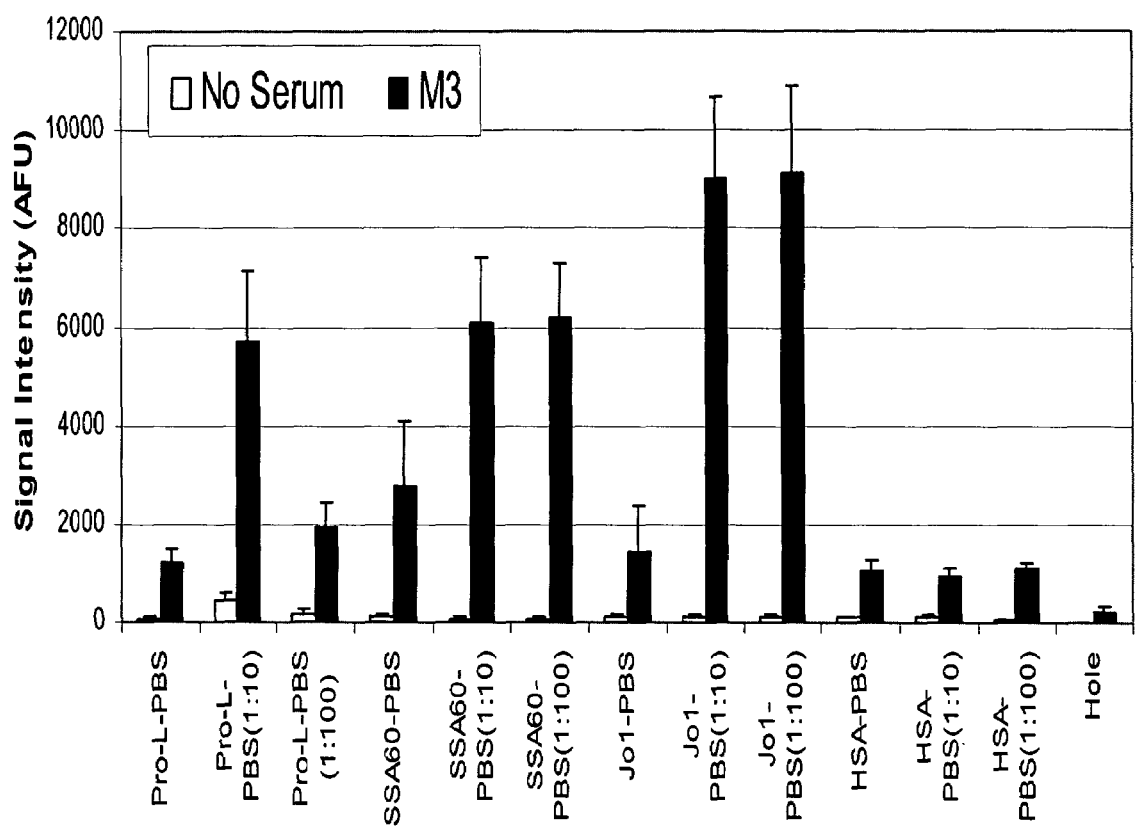
FIG. 6 plots signal intensity from various proteins immobilized in a reaction performed at various salt concentrations and at pH 3.0 on gel-shell beads.

As shown in FIG. 6, the beads coupled using low-salt buffers had significantly higher antibody reactivity compared to the beads coupled at regular PBS, indicating the passive adsorption is more favorable in low ionic strength environment. Similarly, higher antibody reactivities were achieved for proteins including HLA class I, Class II antigens, human IgG, mouse IgG, SSB, and CENP which were immobilized onto beads at low salt and acidic buffer conditions (results not shown).

Example 8

Antigen Panel Coupled through Passive Adsorption for Auto-Antibody Screening and Titration Curve of Disease Positive Serum Samples To evaluate the feasibility of the passively adsorbed proteins for auto-antibody screening, a 6-antigen panel was established by coupling auto-antigens—SSA-60, Sm, Sm/RNP, Jo-1, CENP, and SSB—onto thin-shell beads through passive adsorption under low salt and low pH conditions. Following a blocking procedure with storage buffer containing 0.1% (W/V), these beads were stored individually at 4° C. until they were used.

Figure 7:
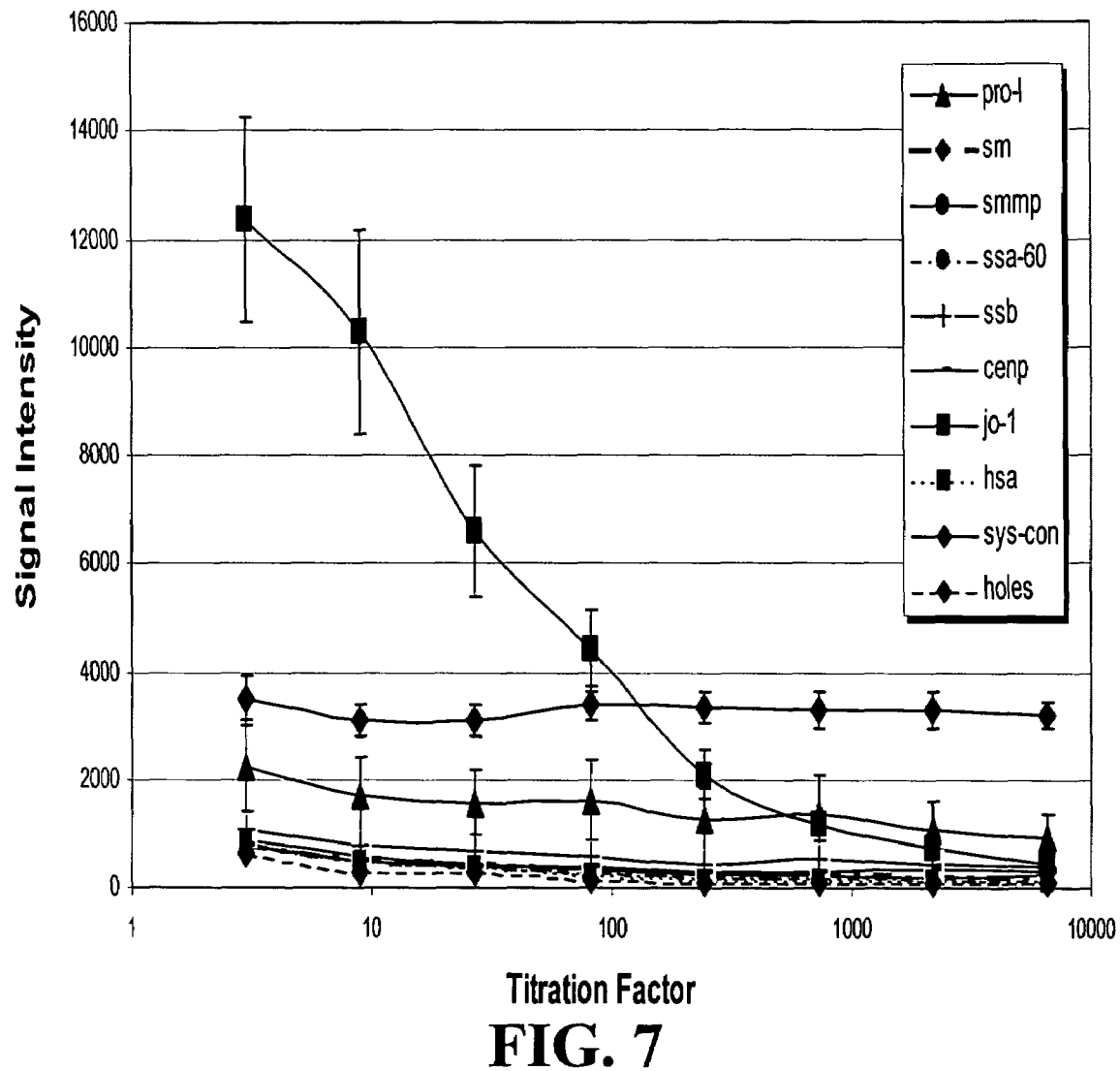
FIG. 7 plots signal intensity from various proteins at various concentrations immobilized in a reaction performed at a relatively low fixed ionic concentration and at pH 3.0 on gel-shell beads.

The beads coupled with various antigens were pooled and assembled on silicon chips. An antibody titration curve was obtained using these chips and a pre-characterized anti-Jo-1 positive serum sample. A serial of diluted serum samples were prepared at 1:3, 1:9, 1:27, 1:81, 1:243, 1:729, 1:2187, 1:6561 ratios. These diluted samples were subsequently incubated with 8 chips for 30 min at room temperature. After removing non-specific bound antibodies, a goat anti-human IgG specific antibody-Alexa conjugate was used to visualize the bound IgG antibodies. The decoding and assay images were collected and the assay signals are then extracted and analyzed. FIG. 7 shows that: (1) Jo-1-coupled thin-shell beads give rise to specific reactivity with background minimal activity, as observed for all other antigen-coupled thin-shell beads, indicating specific antibody-antigen interaction; and (2) the intensity of the anti-Jo-1 reactivity increases in a concentration dependent manner.

Figure 8:
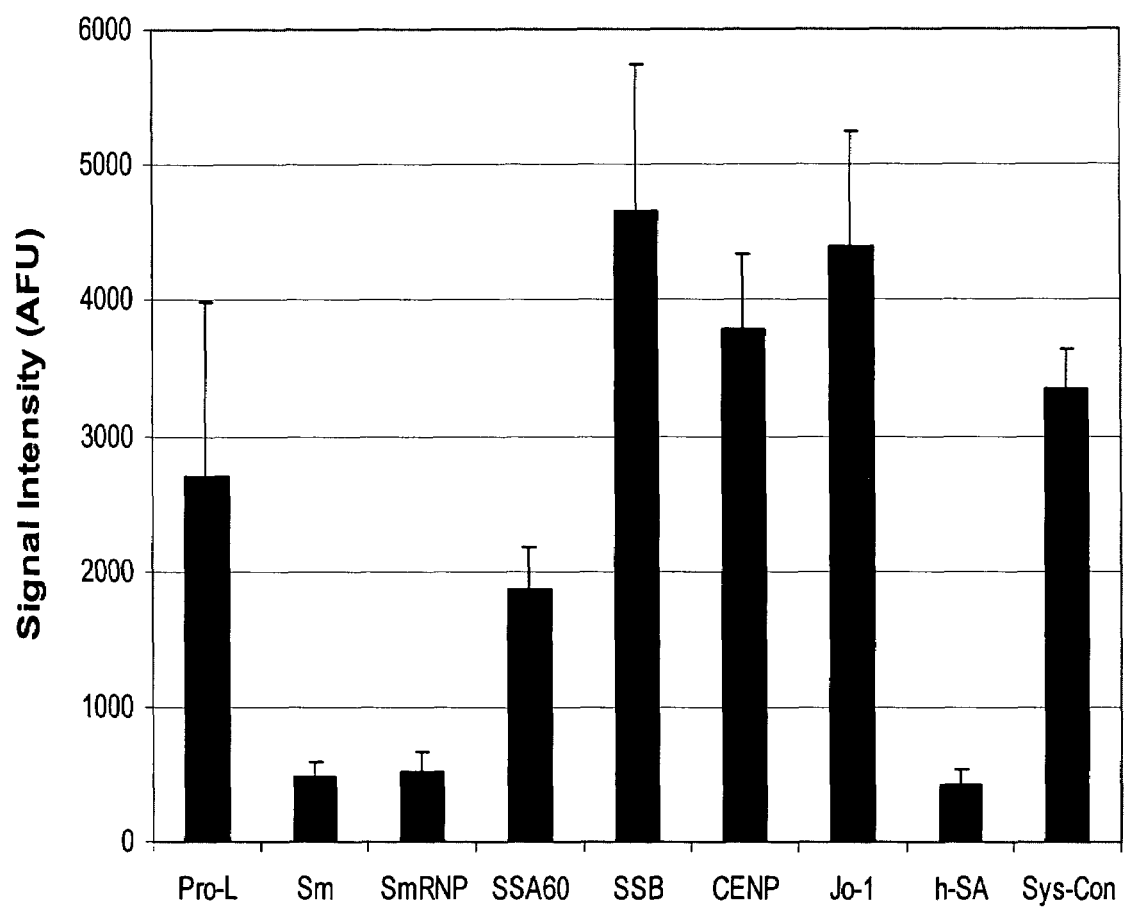
FIG. 8 shows results from reaction of a pooled serum sample containing anti-SSA-60, Anti-SSB, anti-CENP, and anti-Jo-1 antibodies reacted with the antigen panel shown, where the antigens had been adsorbed to gel-shell beads.

Additionally, a pooled serum sample containing anti-SSA-60, Anti-SSB, anti-CENP, and anti-Jo-1 antibodies was reacted with the chip which was coated with the 6-antigen panel. As shown in FIG. 8, strong specific reactivities were observed for beads coupled with SSA-60, SSB, CENP, and Jo-1 antigens, but not for beads coupled with sm, sm/RNP, or a negative control (h-SA; human serum albumin).

Example 9

Protein-Chip Assay Procedure

Protein-Chip Assay Procedure A using Cy5-antibody conjugate:
1. Add 15 uL of prepared serum sample each chip. Place the chips in a humidifying chamber. Incubate at room temperature for 30 min while shaking.
2. Remove the serum sample; wash each chip with 15-20 uL wash buffer (regular PBS with 0.25% (V/V) Tween-20) instantly for three times.
3. Add 15 uL 1-100 diluted goat anti-human IgG gamma specific antibody-Cy5 conjugate. Place the chips in a humid chamber. Incubate at room temperature for 15 min while shaking.
4. Remove the detection antibodies; wash each chip with 15-20 uL wash buffer instantly for three times.
5. Add 10 uL regular PBS each chip. Place a coverslip on top.
6. Acquire the images using the microscope installed with a CCD camera.
7. Data extraction and analysis.

Protein Chip Assay Procedure B using Alexa-antibody conjugate:
1. Add 15 uL of prepared serum sample each chip. Place the chips in a humidifying chamber. Incubate at room temperature for 30 min without shaking.
2. Remove the serum sample; wash each chip with 15-20 uL wash buffer (regular PBS with 0.25% (VN) Tween-20) instantly for three times.
3. Add 15 uL 1-50 diluted goat anti-human IgG gamma specific antibody-Alexa conjugate. Place the chips in a humidifying chamber.

Incubate at room temperature for 15 min without shaking.
4. Remove the detection antibodies; immediately wash each chip with 15-20 uL wash buffer three times.
5. Add 10 uL regular PBS each chip. Place a cover slip on top.
6. Acquire the images using the microscope installed with a CCD camera.
7. Data extraction and analysis.

Example 10

High Salt Effect on Passive Adsorption of Protein onto Gel-Shell Beads

The effect of high salt on protein adsorption onto thin-shell beads was also examined. Two antigens—SCL-70 and Sm (ImmunoVision, Arizona)—were coupled to distinct fluorescently-encoded thin-shell beads in PBS buffers at different salt concentrations. The buffers were adjusted to pH 3 using HCL. Specifically, the reactions were carried out under five different salt conditions (5×, 1×, 0.2×, 0.04×, and 0.008× PBS) for 4 hours at 37° C. The 5× concentrated buffer was 0.5 M Sodium Phosphate; 0.75M Sodium Chloride at pH 7.2. The beads were then blocked with a storage buffer containing 0.1% BSA. These beads were pooled and assembled onto silicon chips.

Figure 9:
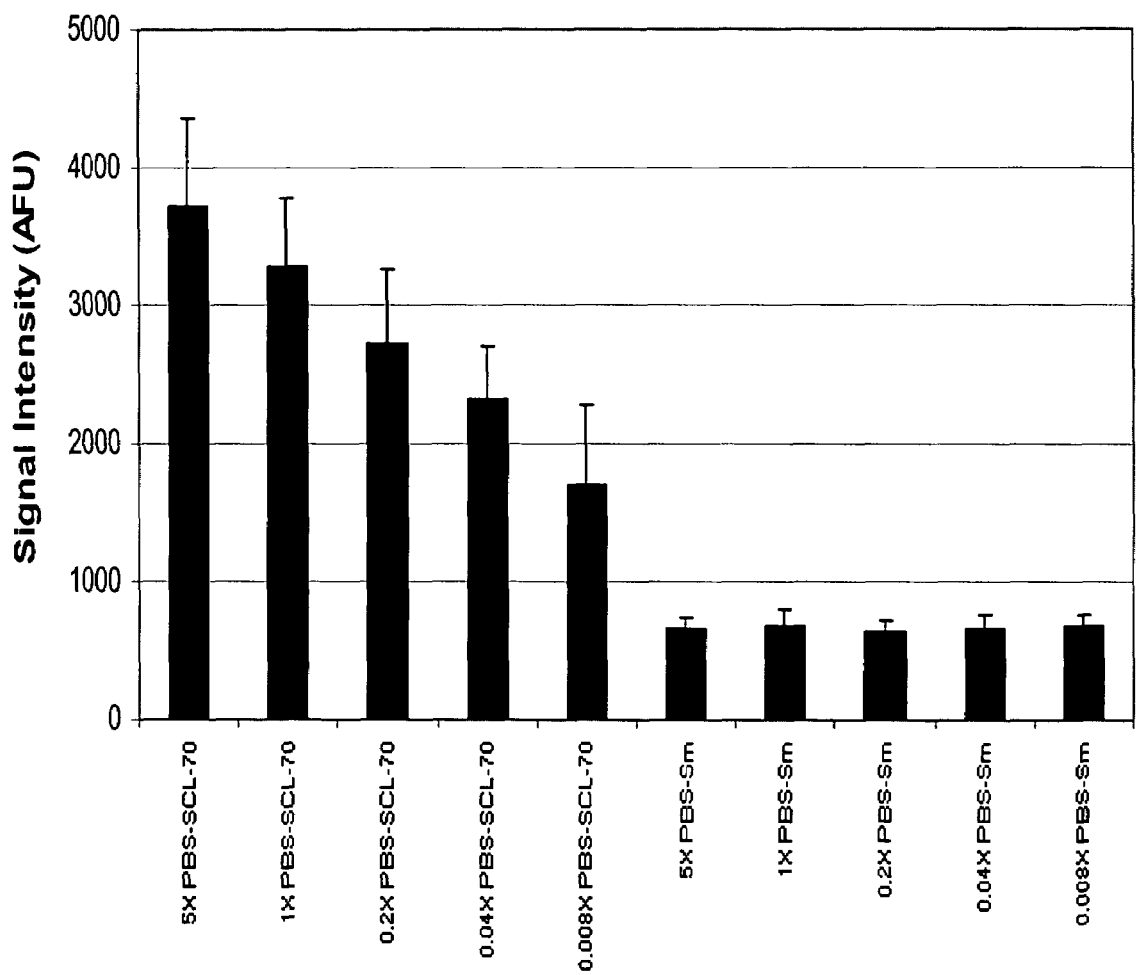
FIG. 9 shows results from reaction of anti-SCL-70 serum with SCL-70 and Sm adsorbed to gel-shell beads at pH 3.0 and at various salt concentrations.
Figure 10:
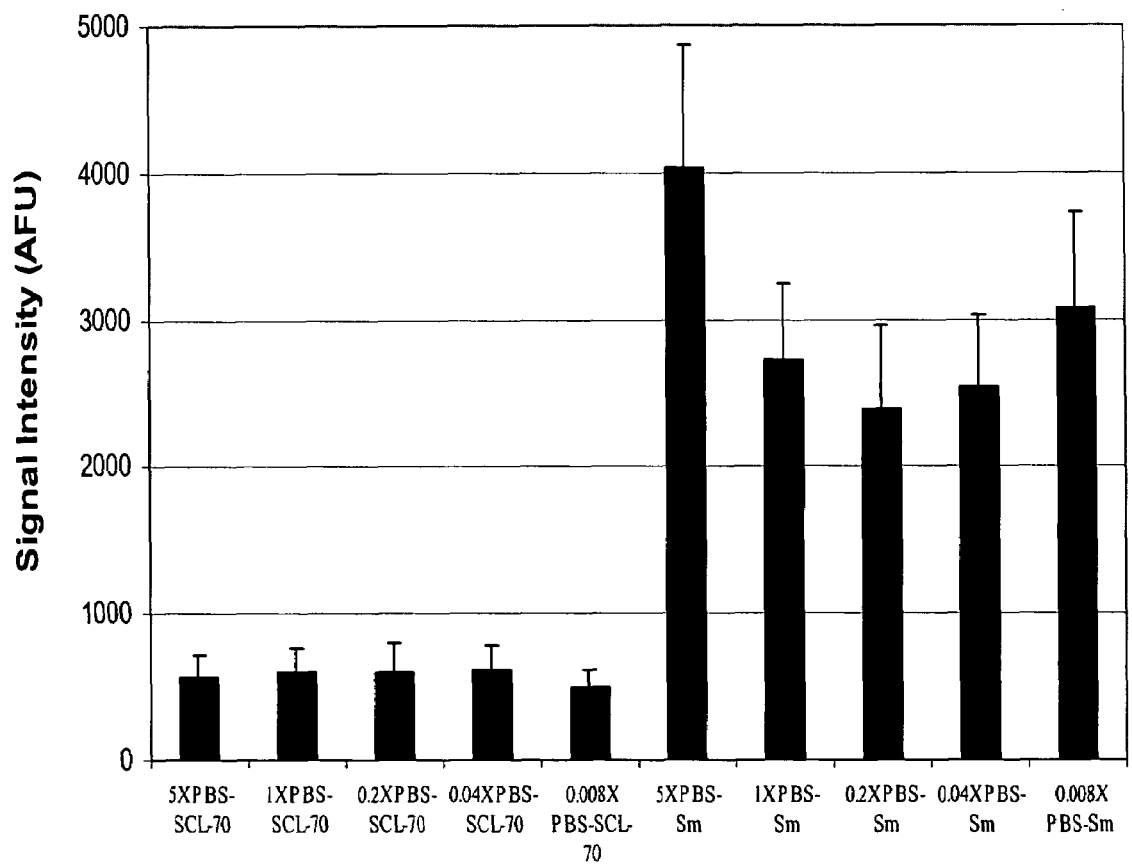
FIG. 10 shows results from reaction of anti-Sm serum with SCL-70 and Sm adsorbed to gel-shell beads at pH 3.0 and at various salt concentrations.

To assess the antibody binding activities of these beads, two well-characterized serum samples (anti-Sm positive or anti-SCL-70 positive) were used. The samples were diluted with assay buffer at 1:10 ratio and subsequently incubated with the chips for 30 min at room temperature. After removing non-specific bound antibodies, the chips were incubated with a goat anti-human IgG specific antibody-Alexa conjugate for 15 min at RT. After a second washing step, the decoding and assay images were acquired and the assay signals were extracted and analyzed. As shown in FIG. 9 (1) specific anti-SCL-70 reactivity was observed with beads coupled with SCL-70 antigen but not the beads coupled with Sm; and (2) the intensity of the anti-SCL-70 reactivity is salt concentration dependent, with the highest activity achieved with beads coupled at 5×PBS. Similarly, the highest anti-Sm reactivity was observed with beads coupled at 5×PBS. See FIG. 9.

Example 11

Immobilization of Enzyme on Gel-Shell Beads and Effects on Enzyme Activity

Experiments were conducted to determine if enzymes which are immobilized on hydrogel core shell beads will lose enzymatic activity. Streptavidin conjugated horseradish peroxidase (streptavidin-HRP) was used as a model enzyme in characterizing the core shell beads. It is well known that streptavidin has high affinity to biotin and biotinylated molecules. Horseradish peroxidase has been widely used as in labeling, conjugated to secondary antibody for detection of antigen-antibody complex in an oxidation reaction, such as a chemilumilescent assay. There are known methods to detect the activity of streptavidin and horseradish peroxidase in the conjugated protein complex.

Streptavidin-HRP was immobilized to color-encoded thin and thick-shell core beads by passive absorption. Briefly, 750 ug of the protein conjugates were incubated with 1 mg of the color-encoded thin and thick-shell beads in a coupling buffer (3 mM sodium chloride, 2 mM sodium phosphate, pH 3.0), overnight at 37° C., with constant rotation. Bovine serum albumin (BSA) was used as a negative control protein. After protein functionalization, the particles were washed by using phosphate-buffered saline (PBS; 0.1 M sodium phosphate, 0.15 M sodium chloride, pH 7.2) with the addition of 0.05% Tween-20 (PBST). Then, all of the functionalized beads were combined into a test tube for assembly onto a silicon chip. The chip binding sites were blocked by using 1% bovine serum albumin (BSA) in PBST prior to use.

Figure 11:
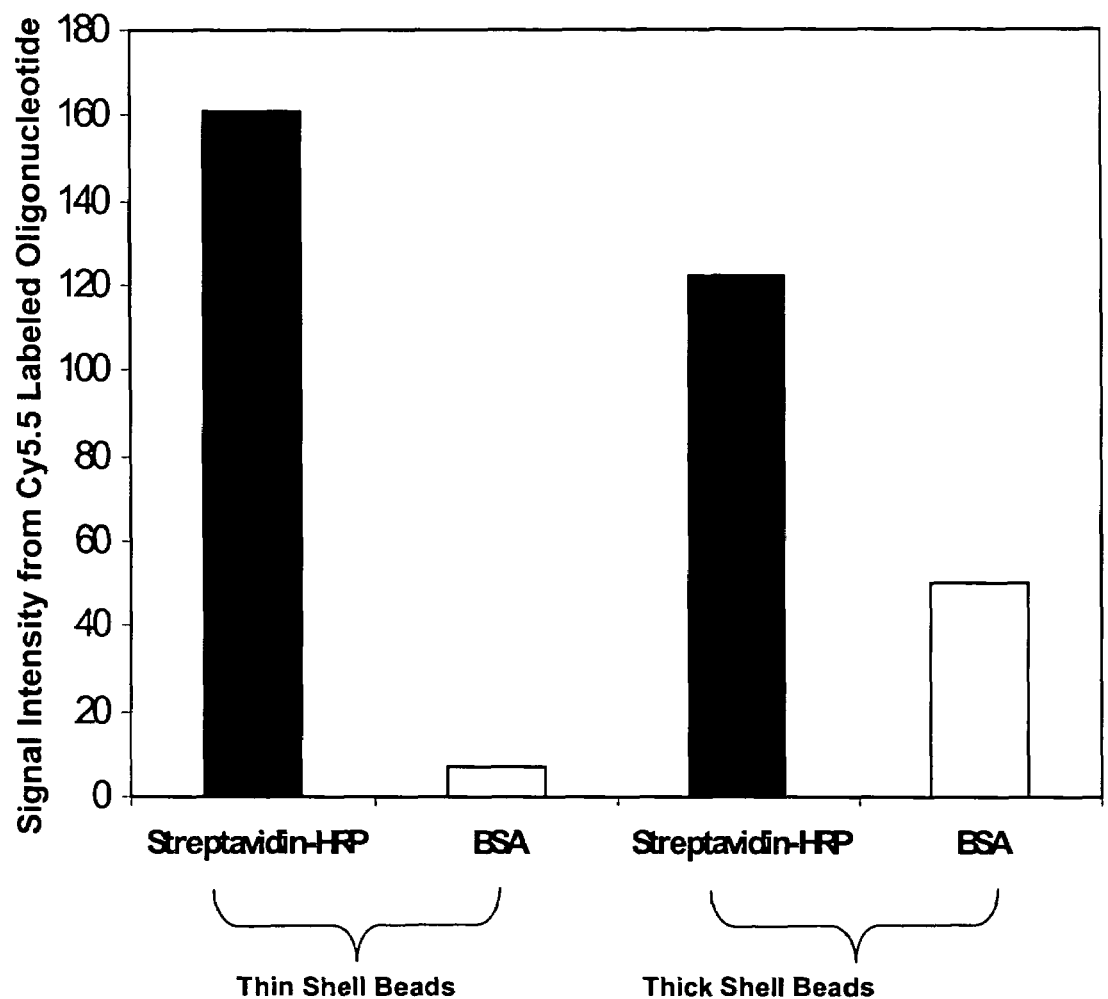
FIG. 11 shows fluorescent signal using a fluorescent biotin target for streptavidin-HRP, and BSA control, immobilized to both thin and thick-shell gel-shell beads by passive absorption.

To verify immobilization of streptavidin-HRP on the beads, the chips were incubated with an oligonucleotide that contains 5 thymine bases labeled with a biotin and a Cy5.5 dye at the 5' and 3' ends, respectively. After incubation, the chip was washed with PBST to remove unbound oligonucleotide, and the signals from the beads were examined using a fluorescent microscope. Cy5.5 fluorescent signal was identified on the streptavidin-HRP coupled beads, indicating immobilization of the protein complex by the beads, without loss of HRP activity (FIG. 11).

Figure 12:
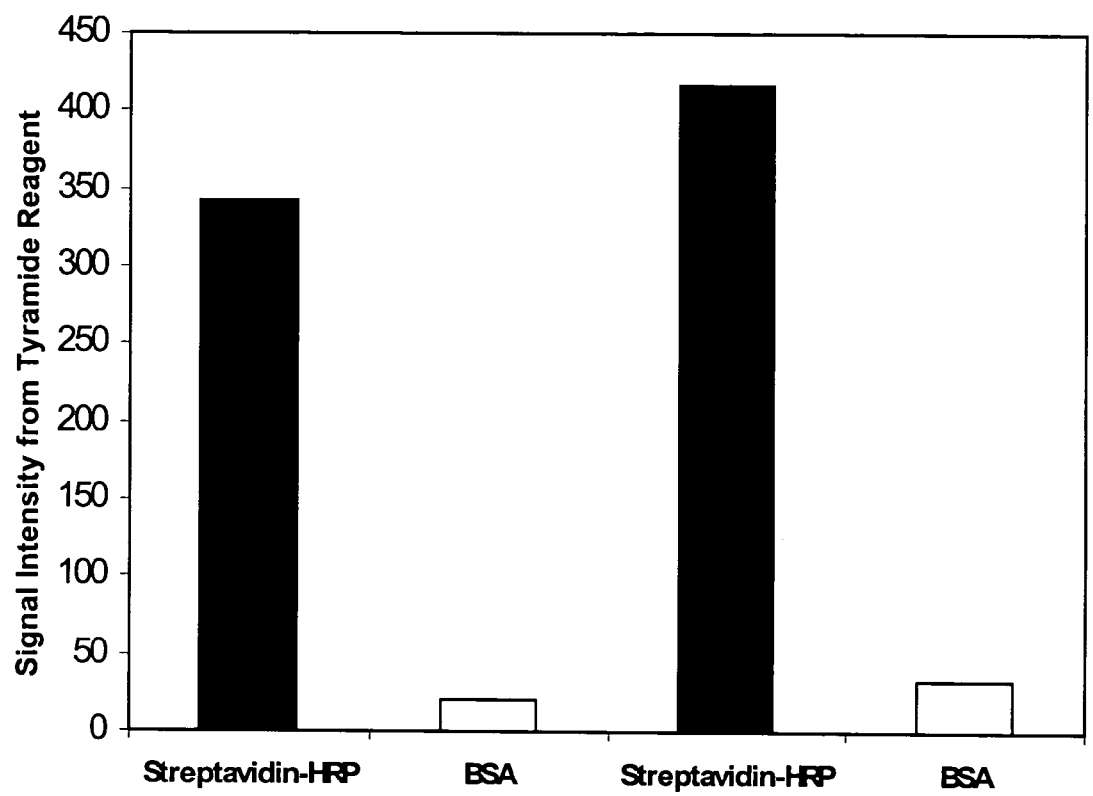
FIG. 12 shows fluorescent signal from streptavidin-HRP, and BSA control, immobilized to both thin and thick-shell gel-shell beads by passive absorption, with signal generated by a different reagent than in FIG. 11.

HRP activity can be determined on streptavidin-HRP coupled core shell beads using known methods, such as tyramide signal amplification technology from Molecular Probes, Inc. (Eugene, OR). In tyramide signal amplification, horseradish peroxidase (HRP) catalyzes activation of fluorescently labeled tyramide to generate highly reactive, short-lived tyramide radicals that can covalently bind to tyrosine residues of vicinity proteins. To summarize the experiments, streptavidin-HRP functionalized beads on a chip were incubated with tyramide reagents (Molecular Probes, Inc. e.g. Catalog # T-20912, T-20916) followed by determination of fluorescent signal on the BeadChip according to known methods. Signal intensity from the Streptavidin-HRP thin and thick-shell beads was significant higher than from the BSA-coated control beads, suggesting that there was peroxidase activity on the beads (FIG. 12).

Example 12

Human Leukocyte Antigens Immobilized on Gel-Shell Beads React with Complementary Antibodies The core shell beads described herein can be used to assay for allo-antibodies specific for human leukocyte antigens (HLA). Human class I and II molecules are two unique classes of HLA antigens expressed in tissue and cells. Class I and II molecules isolated from human cells were immobilized to color encoded core shell hydrogel beads according to the methods described above in Example 4. In parallel, an unrelated protein was coupled to another type of color core shell bead as a negative control. After coupling, all of the functionalized beads were combined and assembly into random planar array on a silicon chip. The chips were then incubated with class I or class II-specific human serum or mouse monoclonal antibodies. Antibodies which bound to HLA antigens on the chips were detected by using fluorescently labeled human or mouse-specific secondary antibodies, and examined by fluorescent microscopy.

Figure 13A:
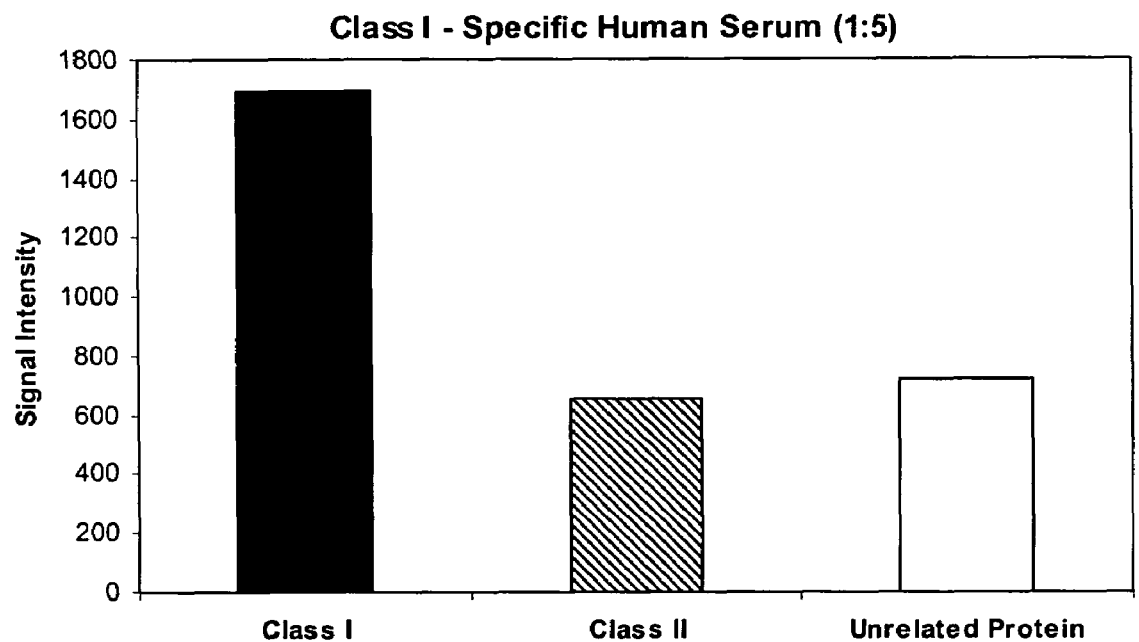
FIG. 13A shows results from adsorption of HLA class I antigen by gel-shell beads, as assayed by specific human serum.
Figure 13B:
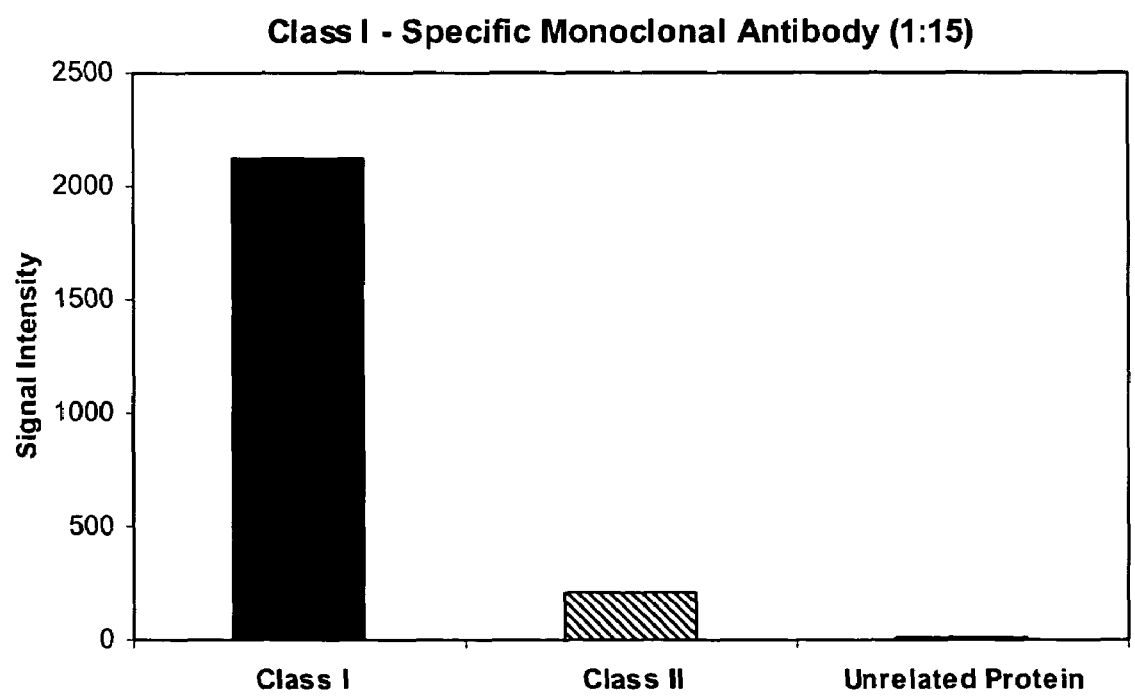
FIG. 13B shows results from adsorption of HLA class I antigen by gel-shell beads, as assayed by an anti-Class I monoclonal antibody.
Figure 13C:
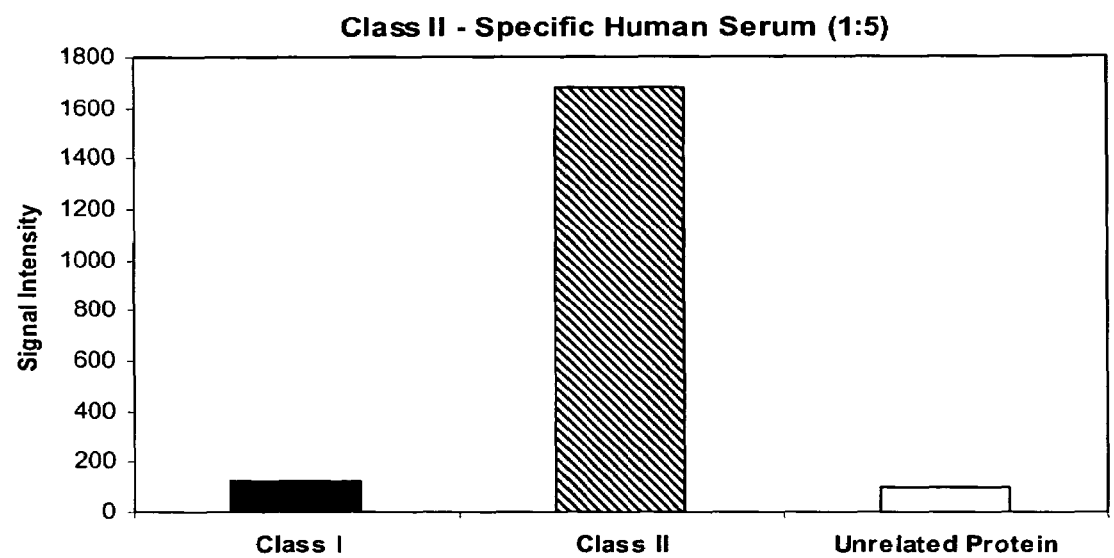
FIG. 13C shows results from adsorption of HLA class II antigen by gel-shell beads, as assayed by specific human serum.
Figure 13D:
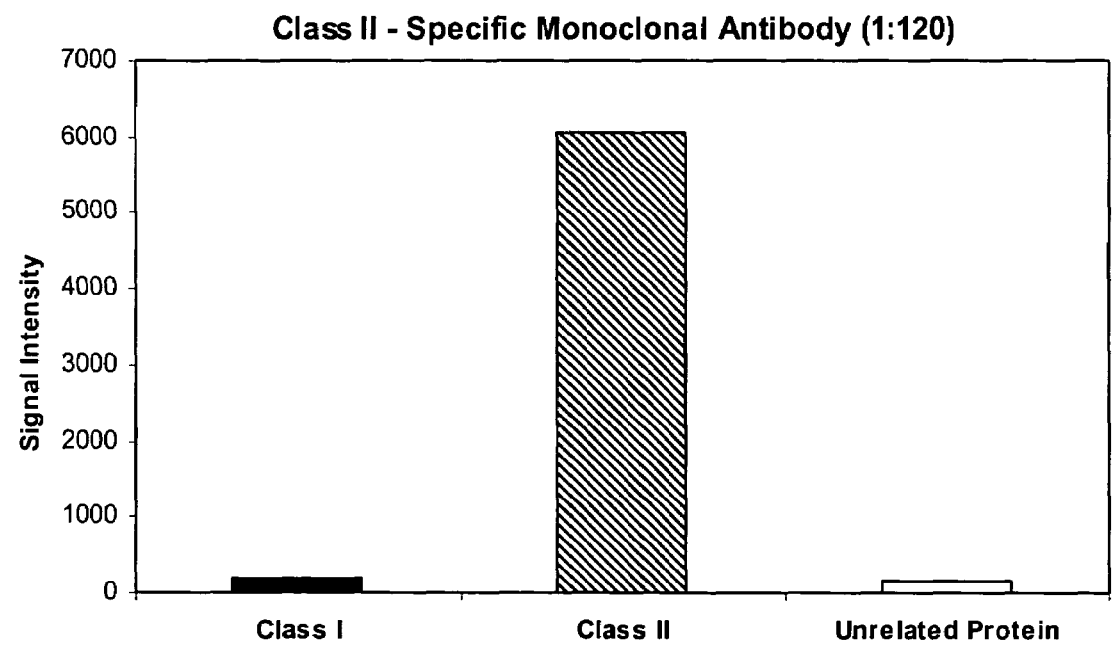
FIG. 13D shows results from adsorption of HLA class II antigen by gel-shell beads, as assayed by an anti-Class II monoclonal antibody.

As shown in FIGS. 13A, 13B, class I and class II-specific human antibodies were identified from core shell beads including the immobilized class I and II antigens, respectively. Specificity of the human antibody binding was further confirmed by using class I and class II-specific mouse monoclonal antibody in the assay (FIGS. 13C, 13D). Class I and II HLA immobilized on core shell beads, therefore, can be used in a panel reactive antibody (PRA) assay in antigen-antibody typing, useful, for example, in determining compatibility for transplantation or transfusion.

III. Covalent Attachment of Protein to Gel-Shell Beads

Example 13

Coupling of Proteins to Carboxylate-Modified Gel-Shell Beads

Figure 14A:
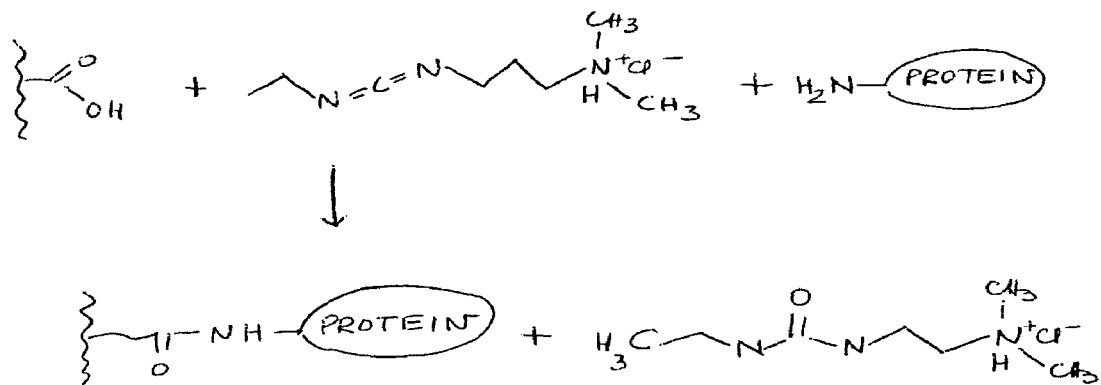
FIG. 14A shows an EDAC-mediated reaction for covalent immobilization of a protein to a functionalized gel-shell.
Figure 14B:
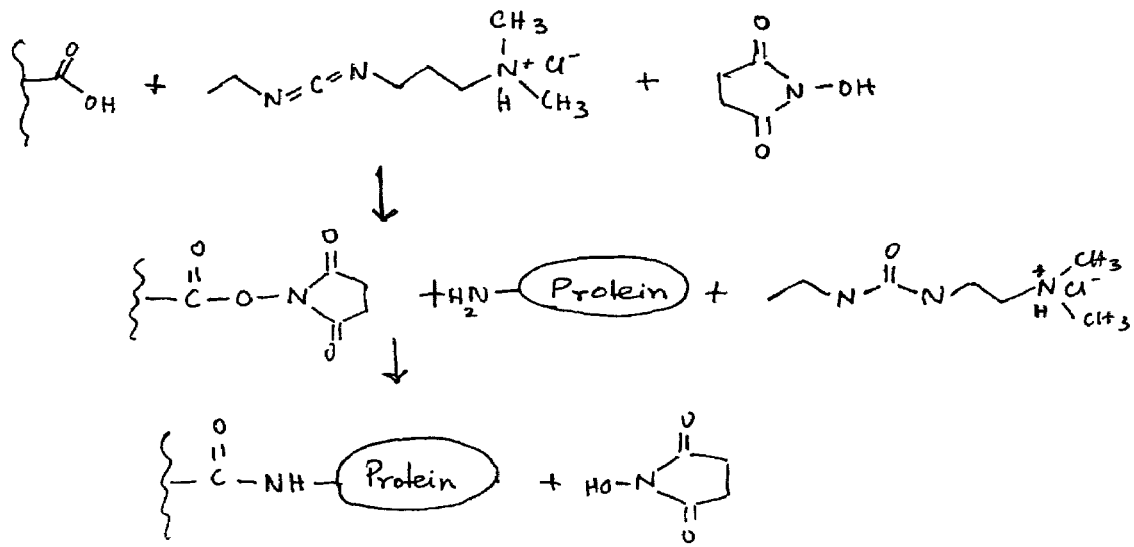
FIG. 14B shows an EDAC-NHS-mediated reaction for covalent immobilization of a protein to a functionalized gel-shell.

Molecules with free amine groups, e.g., proteins, can be coupled to carboxylated beads using a one step carbodiimide (EDAC) reaction (see FIG. 14A). However, for larger molecules water-soluble sulfo-N-hydroxysuccinimide can be added to increase the coupling efficiency (see FIG. 14B). The active ester intermediate formed by the N-hydroxy compound replaces the o-acylisourea intermediate formed otherwise, which is very unstable. The NHS ester is more stable towards hydrolysis but highly reactive towards amines on the protein to be coupled.

A. Procedure for Protein Coupling (EDAC-Reaction)

In a 2 ml vial, an aliquot containing 10 mg of carboxylate-functionalized Hydrogel™-shell microparticles was mixed with 1 ml 10 mM borate buffer (pH=8.5). The particles were then separated by centrifugation and the supernatant was siphoned off. Following this, the separated pellet was washed two times in 0.1M MES buffer (pH=4.5) and finally re-suspended in 600 ul of the same. In a separate vial, a pre-calculated amount of protein was dissolved in 300 ul of the MES buffer and the solution slowly added to the suspension of the polymer microparticles. The suspension was briefly sonicated using a probe sonicator. Following this, 150 ul of a 1-ethyl-3-(3-dimethylaminopropyl)-carbodiimide (Aldrich-Sigma, Milwaukee, Wis.) (EDAC) solution (200 mg/ml) was added to the particle solution. The mixture was allowed to react for 2 hours at room temperature, following which the protein-functionalized polymer microparticles were separated, washed once in coupling buffer, twice in borate buffer and finally re-suspended and stored in storage buffer (PBS pH=7.4, 0.1% (w/v) BSA, 0.5%(w/v) Tween 20, 10 mM EDTA and 0.02% (w/v) NaN$_3$) at 2-8° C. See FIG. 14A B. Procedure for Protein Coupling (EDAC-NHS Reaction)
 1. Add 1 mL of PBST to a 1.5 mL Eppendorf tube.
 2. Transfer 50 µL of 1% carboxylated beads (0.5 mg) to the corresponding tube, and mix well by vortexing.

3. Centrifuge down @ 7500 rpm for 2 min and decant the supernatant.
4. Wash 1× with 1 mL of PBST and 1× with 1 mL of coupling buffer (0.1M MES, 0.15M NaCl solution, pH6.0), and decant the supernatant.
5. Add 30 mg of EDAC and 6 mg of NHS to a 3 mL of coupling buffer, mix completely and add 1 mL of the solution to the tube.
6. Allow to react for 15 min. at room temperature with end-over-end mixing
7. Centrifuge down @ 7500 rpm for 2 min and decant the supernatant.
8. Wash 2× with 1 mL of PBST and 1× with 1 mL of coupling buffer, and decant the supernatant.
9. Dissolve required amount of protein (include details of protein amount) in 0.5 mL of coupling buffer, and mix well.
10. Transfer 500 µL of protein solution in step #9 to the tube containing beads in step 8, mix well and incubate the mixture of protein and bead suspension at 4° C. overnight with mild mixing.
11. Allow to come to room temperature. Quench the reaction by adding 50 µL of ethanolamine to 500 µL volume of reaction solution.
12. Incubate 30 min. at room temperature with end-over-end mixing.
13. Wash 2× with 1 mL of PBST, decant the supernatant, and re-suspend the beads in 50 µL of storage buffer (0.1M PBS containing 0.1% BSA, 0.1% Tween 20 and 0.1% NaN3) at a bead concentration of 10 mg/mL (1% solids). See FIG. 14B A variety of bitoin-binding proteins were coupled to the beads using the protocols outlined above. Neutravidin (a biotin-binding protein, Pierce Chemicals, Rockford, Ill.) was coupled to both thin and thick-shell core beads using the single step EDAC reaction. Mouse Anti-Biotin mAb and Anti-Biotin-Fab (biotin-binding whole and fragmented IgG, Roche Molecular Biochemicals, Indianapolis, Ind.) were coupled using an EDAC-NHS protocol. All the beads were tested for their capture activity as outlined below.

Figure 15A:
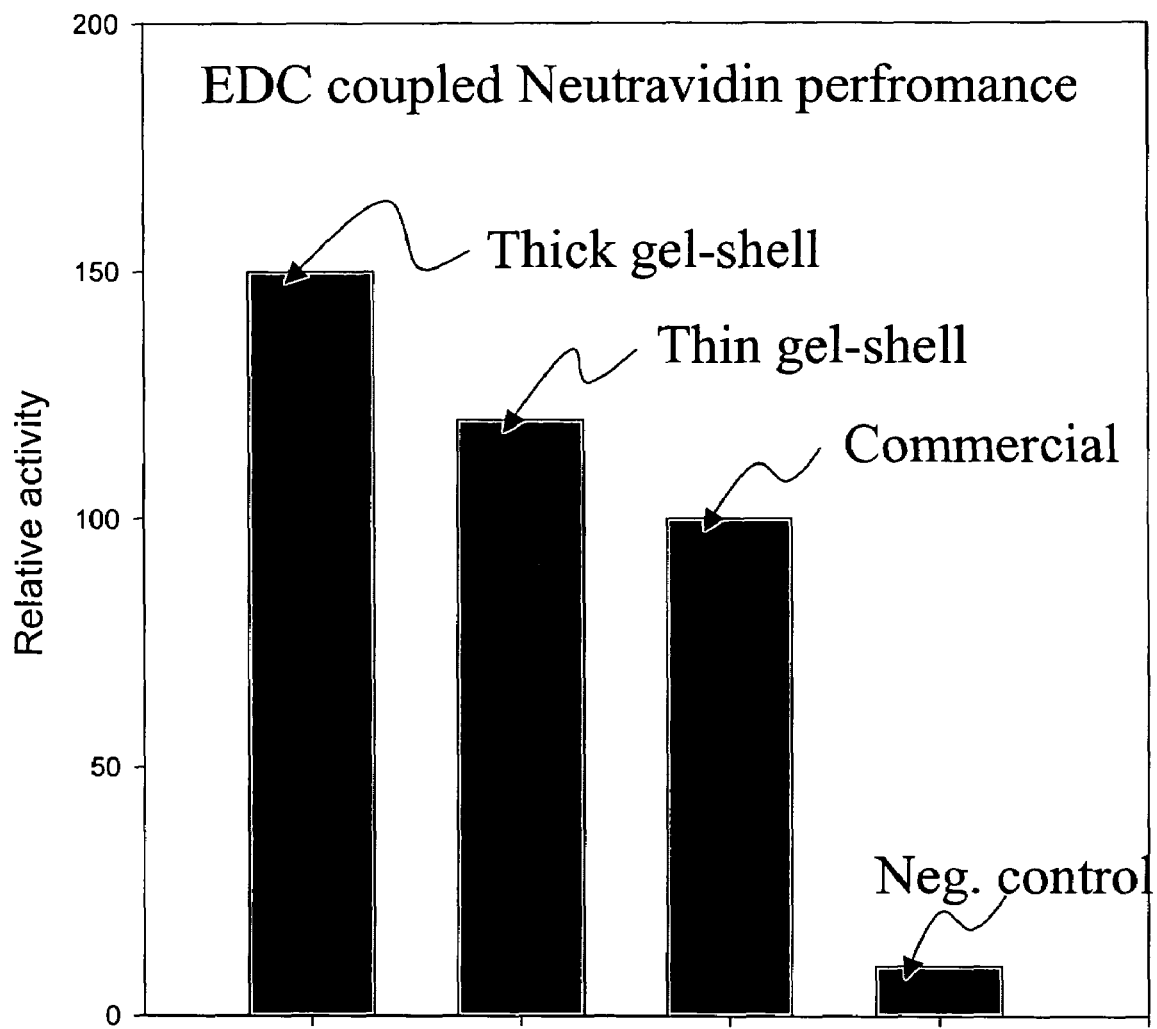
FIG. 15A shows results from Neutravidin coupled to a functionalized gel-shell beads using the single step EDAC reaction.

Biotinylated oligonucleotides with a structure 5'-/5Cy55/TTT TT/3BioTEG/-3' were obtained from IDT (Coralville, Iowa). Beads previously coated with NeutrAvidin™ or other biotin-binding protein were also taken. The binding reaction was carried out in 1% solution of 50 µl of protein-coated particle solution in 0.5 ml reaction buffer (PBS, 0.1 M sodium phosphate and 0.15 M NaCl, pH 7.2) with biotinylated oligo present at a solution concentration of 26.5 ng/µL. The reaction mixture was incubated at room temperature for 30 minutes with vortexing. Upon completion of the binding reaction, the particles were collected by centrifugation, washed three times with PBST (150 mM NaCl, 100 mM sodium phosphate, pH 7.2 with 0.05% Tween-20) and re-suspended in 0.2 ml PBS. The oligonucleotide-functionalized encoded gel-shell particles were then assembled on a silicon substrate and the fluorescence intensity (from the 5' Cy55 fluorophore tag) was analyzed using a fluorescent microscope and assay imaging software developed in-house. The results are shown in FIGS. 15A, 15B, and 15C). In all the cases, for comparison, the same batch of protein was also covalently coupled to commercially available similar sized particles (Bangs Laboratories, Fishers, Ind.). The results show the gel-shell beads perform better or in the worst case as well as the commercial beads.

Separately, an affinity purified SCL-70 protein (Immunovision, Springdale, Ark.) was coupled to gel-shell beads using an EDAC-NHS protocol. In this case also for comparison, the same batch of protein was also covalently coupled to commercially available similar sized particles (Bangs Laboratories, Fishers, Ind.). The beads were reacted with SCL-70 positive sera as described earlier. The results are shown in FIGS. 15D and 15E.

Example 14

Coupling of Proteins to Aldehyde-Modified Gel-Shell Beads

A. Coupling of —COOH Gel-Shell Particles with Amino-Diol Ligand

Prepare a pH adjusted 3-amino-1,2-propanediol ligand [Sigma-Aldrich] solution in 100 mM MES buffer solution (pH=4.5) with the ligand concentration between 0.5 to 1M. (once dissolved the free base needs titration with concentrated acid solution to bring the pH back to 4.5). Take 100 µl of 1% bead suspension, pellet, and wash 2× with 500 µl of the ligand solution. Re-suspend in 1 ml of the ligand solution and vortex and mix well.

In two separate centrifuge tubes weigh out 20 mg and 10 mg EDAC, respectively (bring EDAC to room temperature before weighing). Add 1 ml of the bead suspension prepared as above to the tube containing 20 mg EDAC, vortex to dissolve EDAC and rotate end over end at RT for 30 minutes. Transfer contents to the second centrifuge tube containing 10 mg EDAC and rotate end over end at room temperature for another 1 hr.

Pellet; wash with PBST (3×) and store in PBST (1 ml, 0.1%) at (2-4° C.) until needed for further use.

B. Oxidation of the Amino-Diol Coupled Gel-Shell

Prepare 120 mM Sodiumperiodate ($NaIO_4$) in 20 mM PBS (5× diluted standard BuPH from Pierce). To prepare a 50 ml stock solution weigh out ~1.3 g of the sodium periodate and dissolve it in 50 ml of 20 mM PBS.

Take the 1 ml bead suspension prepared above, pellet, wash 1× with the 500 µl sodium periodate solution and re-suspend in 1 ml of the same. Protect from light and rotate end over end at room temperature for 30 minutes After incubation is over, pellet and wash the beads 2× with PBST and store in the same. [Sonicate briefly (~10 secs) after each wash]

C. Coupling of Protein to the Aldehyde Gel-Shell

Figure 16:
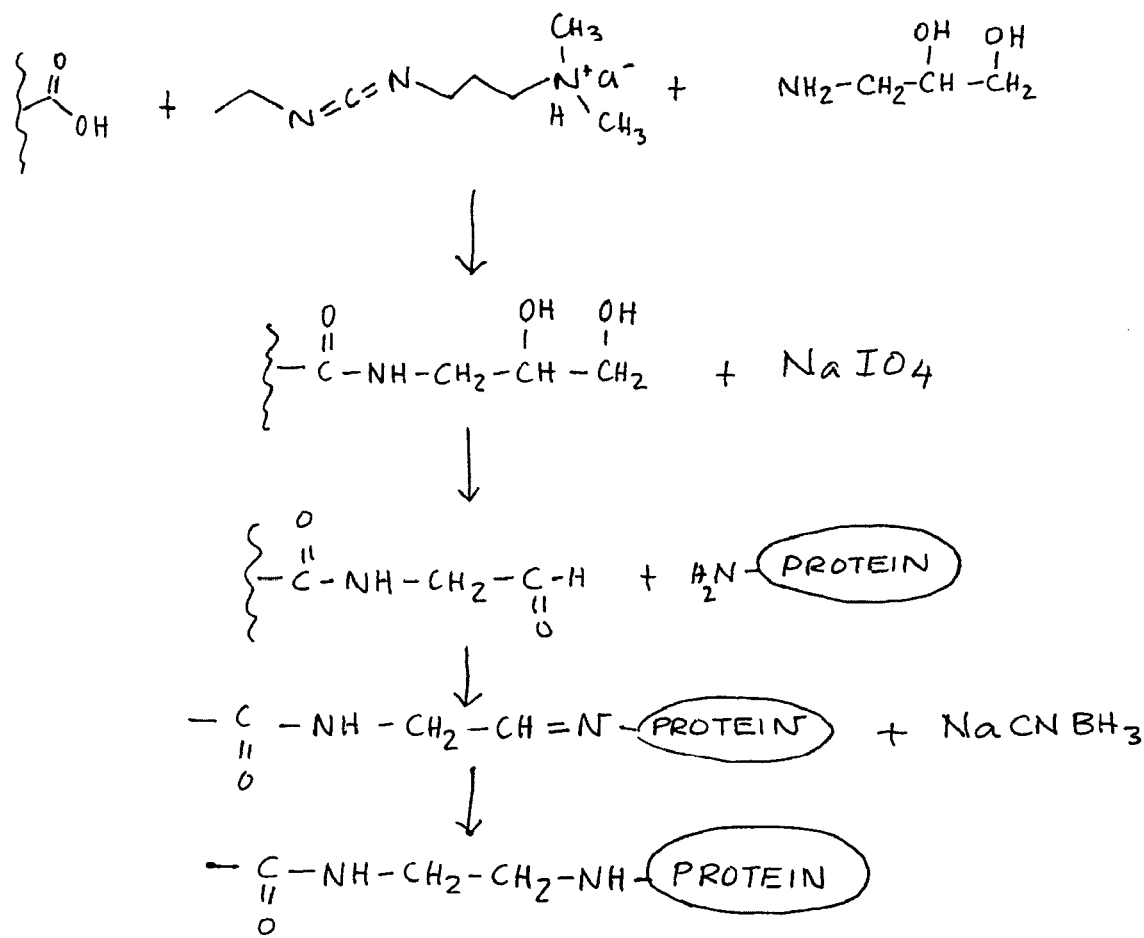
FIG. 16 is an aldehyde-mediated covalent coupling reaction of a protein to a functionalized gel-shell.

Prepare fresh sodium cyano-borohydride solution ($NaCNBH_3$): weigh out 32 mg of sodium cyano borohydride in 0.5 ml of 10 mM Sodium hydroxide (NaOH) [Note: $NaCNBH_3$ is toxic and should be handled under the hood, also, the solution should be prepared more than an hour ahead of time]. See FIG. 16

Take the beads prepared as in subpart B, and pellet and wash 2× with 500 µl PBS. Add 300 µl of PBS, re-suspend, and then add 200 µl of protein solution at a predetermined concentration (made up or as supplied in PBS)(~1 mg/ml). Mix well, add 10 µl of the borohydride solution, protect from light and react with end over end rotation at room temperatute for 2 hours. After incubation, wash 2× with blocking buffer and re-suspend in 500 µl of the same. Store at 2-4° C. until needed for further use.

Figure 17A:
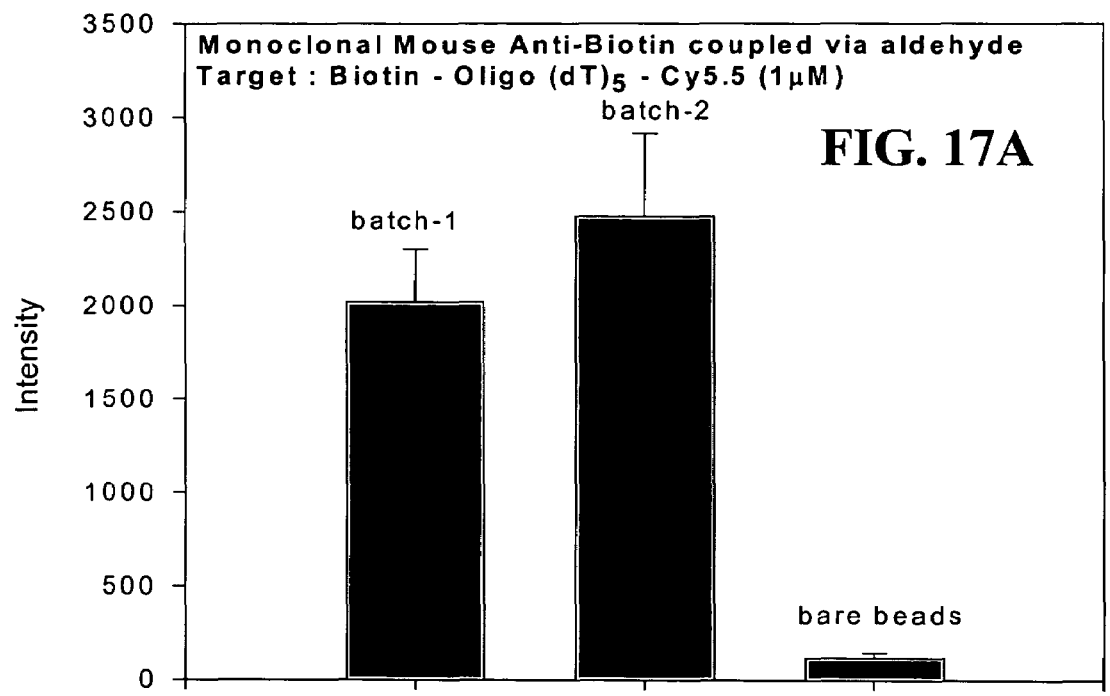
FIGS. 17A and 17B show the results as measured by binding of Biotin-$(dT)_5$-Cy5.5 to mouse anti-biotin antibody immobilized on aldehyde gel-shell beads.
Figure 17B:
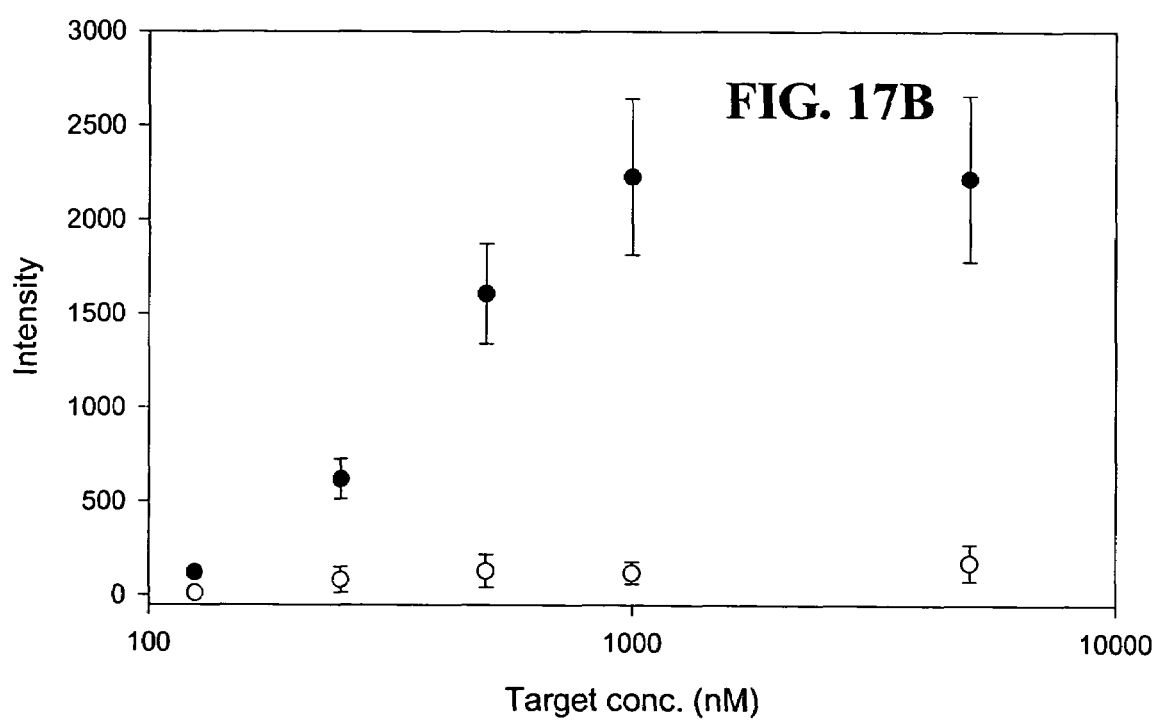
Figure 17C:
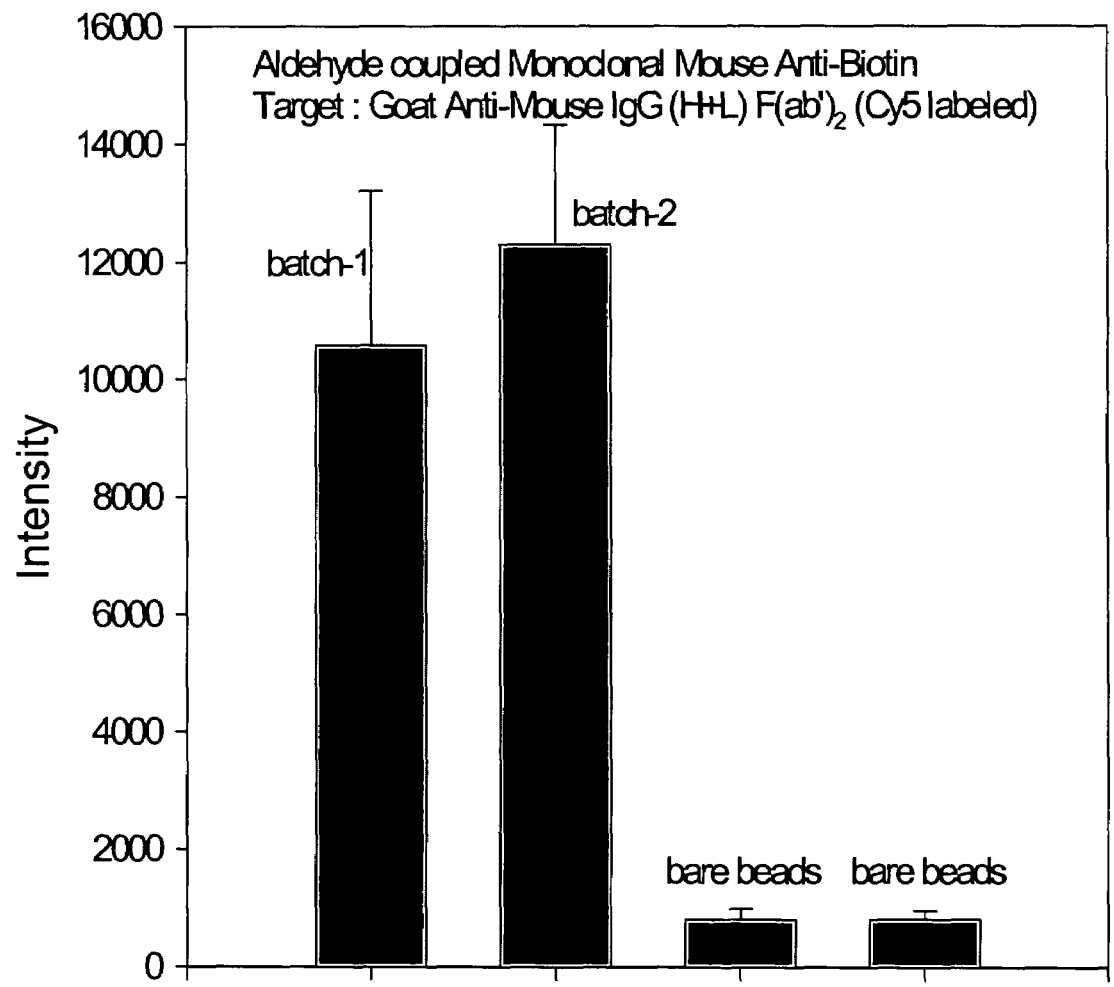
FIG. 17C shows the results as measured by binding of labeled goat anti-mouse IgG to mouse anti-biotin antibody immobilized on aldehyde gel-shell beads.

FIGS. 17A, 17B and 17C shows the assay results using monoclonal mouse anti-biotin antibody (Jackson Immunoresearch, Westgrove, Pa.) immobilized on aldehyde beads. Two types of detection were carried out using a biotinylated Cy5.5 labeled oligonucleotide (5'-/5Cy55/TTT TT/spacer/Biotin/-3') (IDT Inc., Coralville, Ind.) and goat Anti-Mouse IgG (H+L) F(ab')$_2$ (Cy5 labeled) (Jackson Immunoresearch, Westgrove, Pa.). A no antibody control bead (a bare 3-amino-1,2-propanediol functionalized bead) was used as a negative control. In all cases the assay signal was specific and the background binding low. A test was also carried out by exposing the anti-biotin coated beads to goat Anti-Human IgG (F$_c\gamma$) whole molecule (Cy5 labeled) antibody (Jackson Immunoresearch, Westgrove, Pa.). The non specific binding was negligible.

Figure 18:
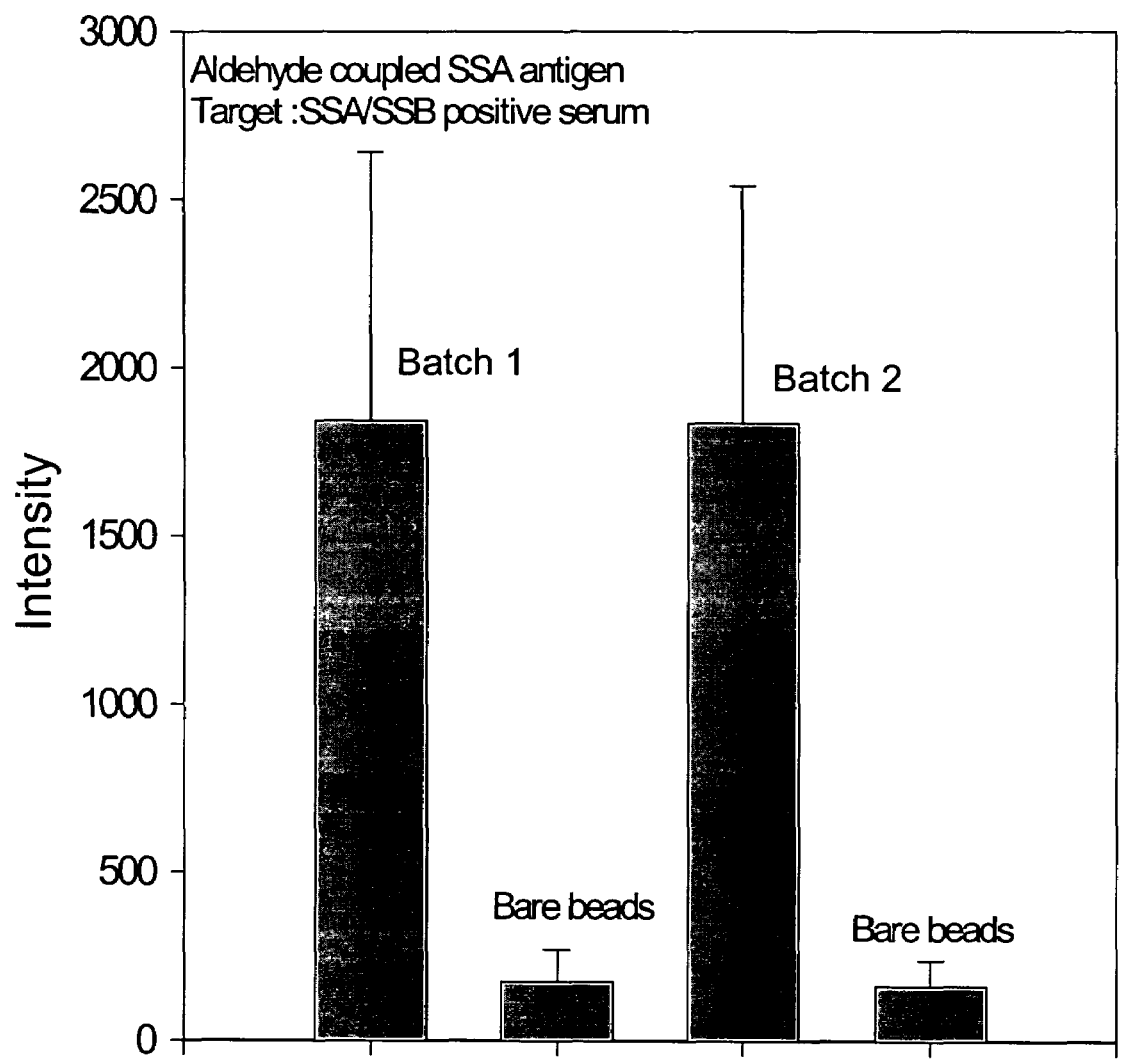
FIG. 18 shows the results using the auto-antigen SSB coated aldehyde gel-shell beads, reacted with SSA/SSB positive sera, and binding detected using labeled anti-human IgG.

FIG. 18 shows the assay results using affinity purified auto-antigen SSB (Immunovision, Springdale, Ark.) beads. The beads were reacted with a SSA/SSB positive sera (1:250 dilution) and the binding detected using Anti-Human IgG (F$_c\gamma$) whole molecule (Cy5 labeled) antibody (Jackson Immunoresearch, Westgrove, Pa.). The reaction was done in duplicate and in each case a no-antigen control bead (a bare 3-amino-1,2-propanediol functionalized bead) was included to access non-specific binding.

Example 15

Coupling of Proteins to Tosyl Modified Gel-Shell

A. Synthesis of Tosylated Ligand

Para-toluene sulfonyl chloride and ethanolamine were obtained from Sigma-Aldrich. 190 mg of tosyl chloride and 60 μl of ethanolamine was added to 10 ml of dry dichloromethane and 250 μl of pyridine added to it. The colorless solution immediately becomes yellow; then the color slowly fades and the solution becomes colorless again. The reaction was allowed to proceed at room temperature for 3 hours, after which the mixture was evaporated to dryness and a sticky viscous paste was obtained as an end product.

B. Coupling of Ligand to Carboxylated Gel-Shell

A pH adjusted 2-amino-1-ethanetosylate solution in 100 mM MES buffer solution (pH=4.5) with the ligand concentration between 0.1 to 1M was prepared. 100 μl of 1% bead suspension, was pelleted, and washed 2× with MES buffer, then re-suspended in 1 ml of the ligand solution ligand solution and vortexed and mixed well. In two separate centrifuge tubes, 20 mg and 10 mg EDAC respectively was weighed out (EDAC brought to room temperature before weighing). 1 ml of the bead suspension prepared in step 1 was added to the tube containing 20 mg EDAC, vortexed to dissolve EDAC and rotated end over end at RT for 30 minutes. Contents were transferred to the second centrifuge tube containing 10 mg EDAC and rotated end over end at room temperature for another 1 hr. Following pelleting, it was washed with PBST (3×) and store in PBST (1 ml, 0.1%) at (2-4° C.) until further use.

C. Coupling of Protein

Figure 19:
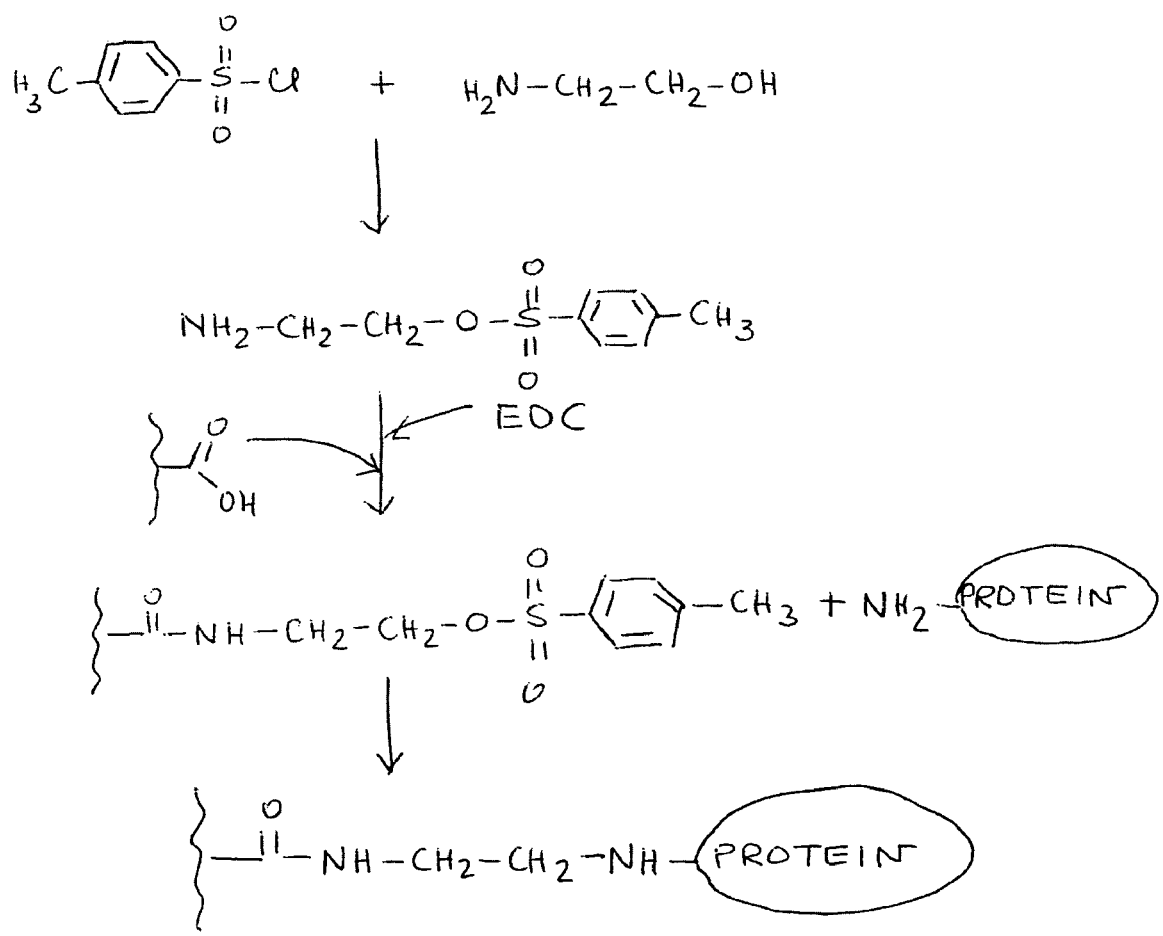
FIG. 19 is a tosyl-mediated covalent coupling reaction of a protein to a functionalized gel-shell.

In a 2 ml vial, an aliquot containing 10 mg of tosyl-functionalized core-shell microparticles was mixed with 1 ml 100 mM borate buffer (pH=9.0). The particles were then separated by centrifugation and the supernatant was siphoned off. Following this, the separated pellet was washed two times in 100 mM borate buffer (pH=9.0) and finally re-suspended in 600 ul of the same. In a separate vial, a pre-calculated amount of protein was dissolved in 300 ul of the borate buffer and the solution slowly added to the suspension of the polymer microparticles. The suspension was briefly sonicated using a probe sonicator. The mixture was allowed to react overnight at 37° C., following which the protein-functionalized polymer microparticles were separated, washed twice in borate buffer and finally re-suspended and stored in storage buffer (PBS pH=7.4, 0.1% (w/v) BSA, 0.5%(w/v) Tween 20, 10 mM EDTA and 0.02% (w/v) NaN$_3$) at 2-8° C. See FIG. 19.

Example 16

Gel-Shell Bead Arrays for Cytokine Monitoring

Another potential use for the gel-shell beads described herein is in carrying out multiplexed assays for cell-secreted cytokines. The strategy involves assembling, on a substrate, arrays of encoded gel-shell microparticles with antibodies immobilized in the gel. Appropriately stimulated cells (also in an array format) are then contacted with (layered on the) the microparticle array in a humidified 37° C. CO$_2$ incubator for a specified period of time. The cells are larger than the microparticles, and therefore each cell tends to be in contact with several different microparticles, and each microparticle is capable of assaying for a different cell product.

Figure 20:
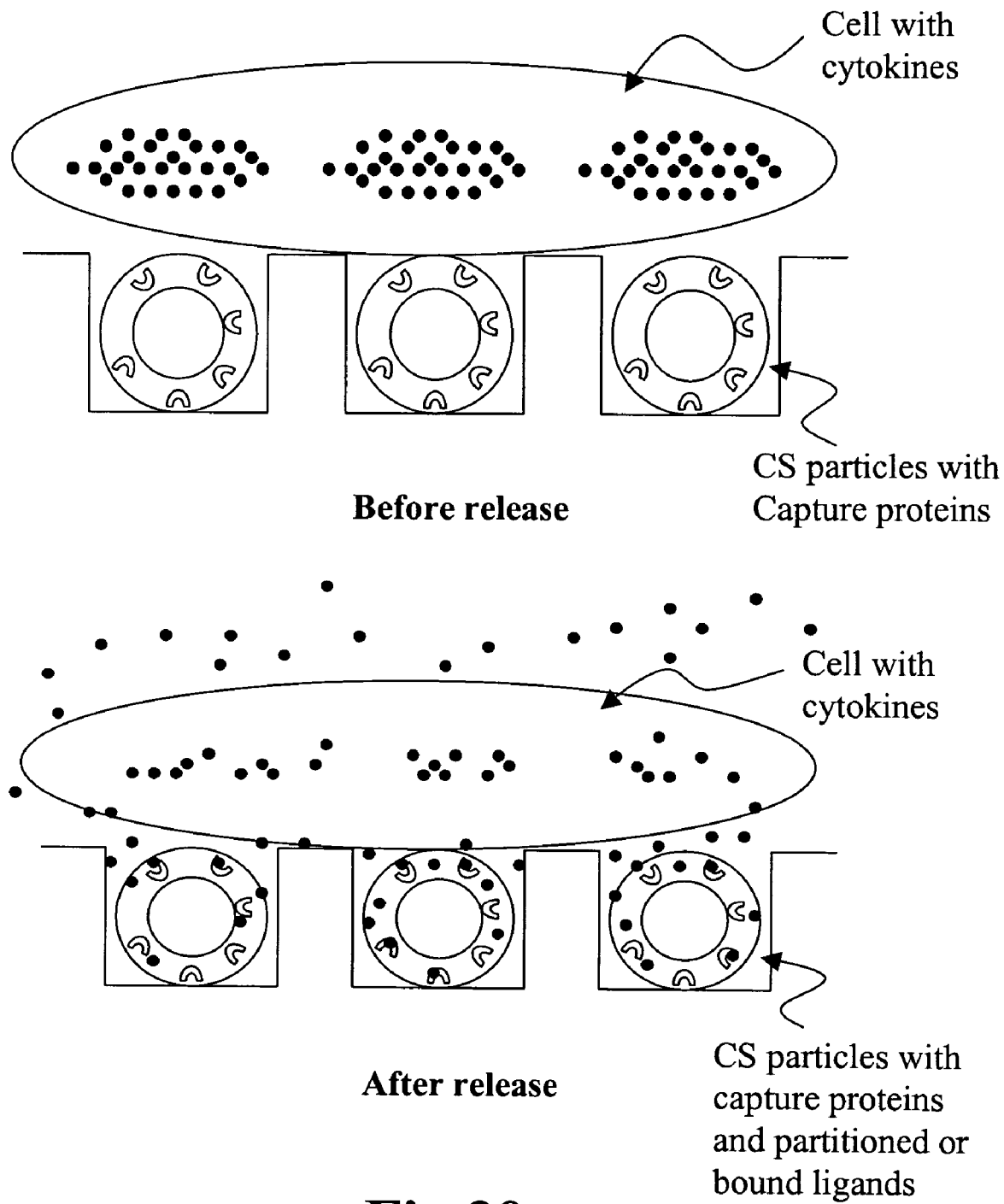
FIG. 20 shows the relative positions of the cells and the beads in an assay format for monitoring and determining cytokine release by cells.

During this incubation period, the cells secrete cytokines, which partition to the immobilized antibody functionalized beads in the immediate vicinity of the secreting cells, and the cytokines are captured. The shell chemistry can be optimized for the partitioning, so as to exclude other large molecules. After removal of the cells and washing away any unbound substances, a cocktail of fluorescently labeled secondary antibodies specific for the chosen cytokines is added to the array. Following a wash to remove any unbound secondary antibody, the array is imaged using a standard fluorescent microscope and the extent and type of cytokine secretion is determined from the recorded fluorescent intensity on the differently encoded microparticles. The relative positions of the cells and the beads in this assay format (before and after cytokine release) are illustrated in FIG. 20.

The advantages of this assay over conventional formats of cytokine analysis is that each cell can be in contact with several microparticles, each of which detects a different cytokine. In this manner, the cytokines secreted from particular cells can be identified in a multiplexed and high throughput manner that is currently not possible.

Example 17

Making Magnetic Gel-Shell Beads

The gel-shell of the beads of the invention can be rendered magnetic using any one of a variety of conventional methods. For example, the gel-shell could be impregnated with a precursor magnetic mineral salt solution. Addition of a reagent and optionally an oxidizer or heat converts the metal salt to crystals of magnetic oxide which are contained throughout the gel shell (see Chang M. U.S. Pat. No. 4,873,102). Magnetic gel-shell beads can also be produced via a two-step process. The first step in the process involves (i) the synthesis of the gel-shell bead whose surface has been appropriately modified and (ii) a surface modified superparamagnetic magnetic nanoparticle. Once synthesized the nanoparticles and the beads are mixed together leading to the deposition and bonding of the nanoparticles on the gel-shell beads. The surface modified magnetic nanoparticles are commercially available from sources such as Molecular Probes (Eugene, Or), Micromod (Rostock, Germany), Chemicell (Berlin, Germany) and Miltenyi Biotech Inc. (Auburn, Calif.) or can be prepared by methods known in the art (Wilson K. S. et al., European Cells and Materials Vol. 3 Suppl. 2, (2002) 206-209; Gruttner, C. and Teller, J. Magn. Magn. Mat. 194 (1999) 8-15). The nanoparticle coating on the beads can be produced using any one of methods known in art (Radtchenko I. L. et al.

Adv. Mater. 2001, 13, No.22 (1684-1687); Graf C. et al. Langmuir 2003, 19, 6693-6700; Margel et al. U.S. Pat. No. 6,103,379; Caruso, F. et al. Adv. Mater. 1999, 11, 950-953; Caruso, F. et al. Chem. Mater. 2001, 13, 109-116).

In this particular example a variation of the layer-by-layer method of polyelectrolyte coating (Caruso, F. et al. Chem. Mater. 2001, 13, 109-116) was employed to produce the magnetic gel-shell particles. Two separate solutions containing 1 mg/ml of Polyallylamine hydrochloride (Mol. Wt. 15,000, Aldrich, Milwaukee, Wis.) and Polyacrylic Acid, Na salt (Mol. Wt. 8,000, Aldrich, Milwaukee, Wis.) was prepared. 5 mg of washed carboxylated gel-shell beads (~3.4 µm in diameter, synthesized as described earlier) was taken in a 1.5 ml eppendorf tube and 500 µl of 1 mg/ml Polyallylamine solution added. The suspension was vortexed and left to mix by end-over-end rotation for 30 mins. Following, the beads were separated via centrifugation and the supernatant discarded. The pellet was washed twice with DI water via centrifugation redispersion cycles. Next, 500 µl of Polyacrylic acid solution was added to the pellet and the suspension mixed via vortexing. The suspension was then treated the same as described before. Alternate cycles of Polyallylamine and Polyacrylic acid were continued till five layers of each were deposited. After the deposition of the fifth Polyallylamine layer, the beads were separated by centrifugation, the pellet washed thoroughly with DI water and dispersed in 500 µl of the same. Next 10 µl of polysaccharide coated carboxyl functionalized nanoparticle (as supplied) was added to the bead suspension (Chemicell, Berlin, Germany), mixed by vortexing and allowed to mix by end-over-end rotation for overnight. The beads were then separated by centrifugation making sure none of the nanoparticles or nanoparticle aggregates not associated with the beads end up in the pellet. The pellet was washed thoroughly with DI water and resuspended in PBST (PBS buffer with 0.1% Tween (v/v) and containing Sodium Azide as a preservative). The particles were magnetic as judged by their migration to the side of a sample tube when placed into a magnetic particle concentrator (Promega, Madison, Wis.). Approximate migration time was 2 minutes.

It should be understood that the terms, expressions and examples used herein are exemplary only, and not limiting, and that the scope of the invention is defined only in the claims which follow, and includes all equivalents of the subject matter of the claims. Process and method steps in the claims can be carried out in any order, including the order set forth in the claims, unless otherwise specified in the claims.

What is claimed is:

1. A method of detecting particular binding molecules in a sample, comprising:
    providing a set of encoded beads wherein, said beads having a core and a shell, where the shell is an ionic hydrogel composed of 6% hydroxyethyl methacrylate, 20% methacrylic acid and 74% methyl methacrylate by weight;
    immobilizing, without covalent bonding, Protein L in the ionic hydrogel using PBS as a buffer where the pH is 3 such that said Protein L is absorbed and trapped in the ionic hydrogel;
    suspending the encoded beads with immobilized Protein L therein, in a PBS buffer of pH 7.2 containing 0.1% BSA and 0.1% sodium azide by weight;
    contacting the beads with said binding molecules; and
    determining whether binding of said binding molecules to said Protein L takes place to thereby detect said particular binding molecules in the sample based on detection of signal from labeling associated with the binding event.

2. The method of claim 1 wherein the binding molecules are antibodies, antigens or enzymes.

3. The method of claim 2, wherein the labeling is with a labeled secondary antibody, or another labeled molecule, which binds to the binding molecules.

4. The method of claim 1 wherein said beads are substantially the same size.

5. The method of claim 4 wherein beads have a coefficient of variation of their mean diameter of about five percent or less.

* * * * *